(12) United States Patent
Nicodemus et al.

(10) Patent No.: US 11,351,255 B2
(45) Date of Patent: *Jun. 7, 2022

(54) TREATMENT OF CANCER WITH THERAPEUTIC MONOCLONAL ANTIBODY SPECIFIC FOR A TUMOR ASSOCIATED ANTIGEN AND AN IMMUNE ADJUVANT

(71) Applicant: Oncoquest INC., Edmonton (CA)

(72) Inventors: Christopher F. Nicodemus, Charlestown, MA (US); Ragupathy Madiyalakan, Edmonton (CA)

(73) Assignee: Oncoquest Inc., Edmonton (CA)

( * ) Notice: Subject to any disclaimer, the term of this patent is extended or adjusted under 35 U.S.C. 154(b) by 216 days.

This patent is subject to a terminal disclaimer.

(21) Appl. No.: 16/702,323

(22) Filed: Dec. 3, 2019

(65) Prior Publication Data
US 2020/0101159 A1    Apr. 2, 2020

Related U.S. Application Data

(63) Continuation of application No. 15/654,415, filed on Jul. 19, 2017, now Pat. No. 10,537,636, which is a continuation of application No. 15/470,733, filed on Mar. 27, 2017, now abandoned.

(60) Provisional application No. 62/455,114, filed on Feb. 6, 2017.

(51) Int. Cl.
| | |
|---|---|
| *A61K 39/395* | (2006.01) |
| *C07K 16/28* | (2006.01) |
| *C07K 16/30* | (2006.01) |
| *A61K 31/282* | (2006.01) |
| *A61K 39/39* | (2006.01) |
| *A61K 31/337* | (2006.01) |
| *A61K 31/555* | (2006.01) |
| *A61P 35/00* | (2006.01) |
| *A61K 39/00* | (2006.01) |
| *C07K 14/47* | (2006.01) |

(52) U.S. Cl.
CPC ...... *A61K 39/39558* (2013.01); *A61K 31/282* (2013.01); *A61K 31/337* (2013.01); *A61K 31/555* (2013.01); *A61K 39/00117* (2018.08); *A61K 39/39* (2013.01); *A61K 39/3955* (2013.01); *A61P 35/00* (2018.01); *C07K 14/4748* (2013.01); *C07K 16/2818* (2013.01); *C07K 16/2827* (2013.01); *C07K 16/3069* (2013.01); *C07K 16/3092* (2013.01); *A61K 2039/505* (2013.01); *A61K 2039/507* (2013.01); *A61K 2039/545* (2013.01); *A61K 2039/55516* (2013.01); *A61K 2039/55561* (2013.01); *A61K 2039/55583* (2013.01); *A61K 2039/585* (2013.01); *C07K 2317/24* (2013.01); *C07K 2317/52* (2013.01); *C07K 2319/30* (2013.01)

(58) Field of Classification Search
CPC ........... A61K 31/282; A61K 31/337; A61K 39/3955; A61K 39/39558; A61K 2039/505; A61K 2039/545; A61K 2039/585; C07K 14/4748; A61P 37/04
See application file for complete search history.

(56) References Cited

U.S. PATENT DOCUMENTS

| | | | |
|---|---|---|---|
| 4,816,567 A | 3/1989 | Cabilly et al. | |
| 5,091,513 A | 2/1992 | Huston et al. | |
| 5,225,539 A | 7/1993 | Winter | |
| 5,258,498 A | 11/1993 | Huston et al. | |
| 8,038,994 B2 | 10/2011 | Schultes et al. | |
| 10,537,636 B2 * | 1/2020 | Nicodemus | C07K 16/3069 |
| 2007/0073047 A1 | 3/2007 | Kandasamy et al. | |

FOREIGN PATENT DOCUMENTS

| | | |
|---|---|---|
| EP | 0173494 A2 | 3/1986 |
| EP | 0184187 A2 | 6/1986 |
| EP | 011496 B1 | 5/1993 |
| EP | 0125023 B2 | 3/2002 |
| WO | 8601533 A1 | 3/1986 |
| WO | 8702671 A1 | 5/1987 |
| WO | 9013678 A1 | 11/1990 |
| WO | 2008/091643 A2 | 7/2008 |

OTHER PUBLICATIONS

Antibodies—A Laboratory Manual, Harlow and Lane, eds., Ed Greenfield, Editor, Cold Spring Harbor Laboratory Press: Cold Spring Harbor, New York, 1988.
Beidler et al., "Cloning and High Level Expression of a Chimeric Antibody with Specificity for Human Carcinoembryonic Antigen," 1988 J. Immunol., 141:4053-4060.
Berek, et al., "Oregovomab Maintenance Monoimmunotherapy Does Not Improve Outcomes in Advanced Ovarian Cancer," Journal of Clinical Oncology, vol. 27, No. 3, Jan. 20, 2009, 418-425.
Better et al., "*Escherichia coli* Secretion of an Active Chimeric Antibody Fragment," (1988 Science, 240:1041-1043).
Bookman M., "GOG0182-ICON5: 5-Arm Phase III Randomized Trial of Paclitaxel (P) and Carboplatin (C) vs Combinations with Gemcitabine (G), PEG-Liposomal Doxorubicin (D), or Topotecan (T) in patients (pts) with Advanced-Stage Epithelial Ovarian (EOC) or Primary Peritoneal (PPC) Carcinoma," J Clin Oncol. 2006;24(18S):5002-5002.

(Continued)

*Primary Examiner* — Hong Sang
(74) *Attorney, Agent, or Firm* — Kilpatrick Townsend & Stockton LLP

(57) ABSTRACT

The present document describes a method of inhibiting cancer tumor growth in a patient in need thereof, comprising at least a first treatment comprising steps a) and b): a) administering to the patient an immune adjuvant in combination with a therapeutic monoclonal antibody specific for a tumor associated antigen; and b) administering to the patient the immune adjuvant; and a final treatment consisting of administering to the patient the therapeutic monoclonal antibody specific for a tumor associated antigen, wherein time between step a) and step b) is a time sufficient for treatment of the patient with the immune adjuvant, and wherein time between the step b) and the final treatment is from about 10 to about 14 weeks.

11 Claims, 12 Drawing Sheets

(56) References Cited

OTHER PUBLICATIONS

Braly et al.: "The Immune Adjuvant Properties of Front-line Carboplatin-Paclitaxel: A Randomized Phase 2 Study of Alternative Schedules of Intravenous Oregovomab Chemoimmunotherapy in Advanced Ovarian Cancer", Journal of Immunotherapy. 2009; vol. 32, pp. 54-65.

Cole et al., "The EBV-hybridoma technique and its application to human lung cancer," 1985, in Monoclonal Antibodies and Cancer Therapy, Alan R. Liss, Inc., pp. 77-96.

Cole, et al. "A strategy for the production of human monoclonal antibodies reactive with lung tumor cell lines." Cancer research 44, No. 7 (1984): 2750-2753.

Cote et al., "Generation of Human Monoclonal Antibodies Reactive with Cellular Antigens," 1983, Proc. Natl. Acad. Sci. U.S.A., 80:2026-2030.

Daniels-Wells et al., "A novel IgE antibody targeting the prostate-specific antigen as a potential prostate cancer therapy," Research Article, BioMed Central, BMC Cancer 2013, 13:195.

Drerup et al.: "Immunotherapy for Ovarian Cancer", Current Treatment Options in Oncology. 2015; pp. 1-20.

Gordon et al., "CA125- and tumor-specific T-cell responses correlate with prolonged survival in oregovomab-treated recurrent ovarian cancer patients", Gynecologic Oncology. 2004; vol. 94, pp. 340-351.

Helguera G, et al., "Antibody-Cytokine Fusion Proteins for the Therapy of Cancer," Methods Mol. Med. (2005) 109:347-74.

Jones et al., "Replacing the Complementarity-Determining Regions in a Human Antibody with Those from a Mouse," 1986 Nature, 321:552-525.

Köhler et al., "Continuous Cultures of Fused Cells Secreting Antibody of Predefined Specificity," Journal of Immunology, Nature vol. 256, Aug. 7, 1975; 495-497.

Kozbor et al., "The Production of Monoclonal Antibodies from Human Lymphocytes," 1983, Immunology Today, 4:72.

Liu et al., "Chimeric Mouse-Human IgG1 Antibody that can Mediate Lysis of Cancer Cells," (1987) PNAS, 84:3439-3443.

Liu et al., 1987, "Production of a Mouse-Human Chimeric Monoclonal Antibody to CD20 with Potent Fc-Dependent Biologic Activity," J. Immunol., 139:3521-3526.

Lynch, et al. "Ipilimumab in combination with paclitaxel and carboplatin as first-line treatment in stage IIIB/IV non-small-cell lung cancer: results from a randomized, double-blind, multicenter phase II study." Journal of clinical oncology 30, No. 17 (2012): 2046-2054.

Morrison et al., "Isolation of Transformation-Deficient *Streptococcus pneumonia* Mutants Defective in Control of Competence, Using Insertion-Duplication Mutagenesis with the Erythromycin Resistance Determinant of pAMβ1," 1984, J. Bacteriol. 159:870-876.

Morrison, S. "Transfectomas Provide Novel Chimeric Antibodies," (1985) Science, 229:1202-1207.

Neuberger et al., "Recombinant Antibodies Possessing Novel Effector Functions," 1984, Nature 312:604-608.

Nishimura et al., "Recombinant Human-Mouse Chimeric Monoclonal Antibody Sepcific for Common Acute Lymphocytic Leukemia Antigen," 1987, Canc. Res., 47:999-1005.

Quest Pharmatech: "A Controlled Study of the Effectiveness of Oregovomab (Antibody) Plus Chemotherapy in Advanced Ovarian Cancer", Clinical Trials. May 30, 2012; retrieved from the Internet: https://clinicaltrials.gov/ct2/show/NCT01616303, retrieved on Sep. 18, 2017.

Reck, et al. "Ipilimumab in combination with paclitaxel and carboplatin as first-line therapy in extensive-disease-small-cell lung cancer: results from a randomized, double-blind, multicenter phase 2 trial." Annals of Oncology 24, No. 1 (2012): 75-83.

Santoiemma, et al. "Tumor infiltrating lymphocytes in ovarian cancer." Cancer biology & therapy 16, No. 6 (2015): 807-820.

Shaw et al., "Mouse/Human Chimeric Antibodies to a Tumor-Associated Antigen: Biologic Activity of the Four Human IgG Subclasses," 1988, J. Natl Cancer Inst., 80:1553-1559.

Sun et al. "Chimeric Antibody with Human Constant Regions and Mouse Variable Regions Directed Against Carcinoma-Associated Antigen 17-1A," (1987) PNAS, 84:214-218.

Takeda et al., "Construction of Chimaeric Processed Immunoglobulin Genes Containing Mouse Variable and Human Constant Region Sequences," 1985, Nature 314: 452-454.

Verhoeyan et al., "Reshaping Human Antibodies: Grafting an Antilysozyme Activity," 1988 Science, 239:1534.

Wood et al., "The Synthesis and in vivo Assembly of Functional Antibodies in Yeast," (1985) Nature, 314:446-449.

* cited by examiner

TREATMENT OF CANCER WITH THERAPEUTIC MONOCLONAL ANTIBODY SPECIFIC FOR A TUMOR ASSOCIATED ANTIGEN AND AN IMMUNE ADJUVANT

CROSS-REFERENCE TO RELATED APPLICATIONS

This application is a continuation of U.S. patent application Ser. No. 15/654,415, filed Jul. 19, 2017 which is a continuation of U.S. patent application Ser. No. 15/470,733, filed Mar. 27, 2017 which claims the benefit of priority to US Provisional Patent Application No. 62/455,114 filed on Feb. 6, 2017, the contents of all of the above are hereby incorporated by reference in their entireties.

BACKGROUND

(A) Field

The subject matter disclosed generally relates to methods of inhibiting cancer tumor growth in a patient in need thereof. More specifically, the subject matter disclosed relates to methods of inhibiting cancer tumor growth in a patient by administering a first treatment comprising administering a therapeutic monoclonal antibody specific for a tumor associated antigen in combination with an immune adjuvant; and then administering to an immune adjuvant, followed by a final treatment with the therapeutic monoclonal antibody specific for a tumor associated antigen.

(b) Related Prior Art

Ovarian cancer is the most common cause of gynecologic cancer deaths in the United States. Cytotoxic therapy produces high initial response rates; however, recent intergroup study involving more than 4000 patients was unable to improve progression-free (PFS) or overall survival in any of the 4 experimental combinations that added a third drug with documented single agent activity to the standard front-line treatment [Bookman M. GOG0182-ICON5: J Clin Oncol. 2006; 24(18S):256s; Braly et al. (J Immunother 2009; 32:54-65].

It is well established that aberrant expression of membrane mucin MUC16 (also known as CA125) is associated with tumor progression and metastasis of cancers such as ovarian and pancreatic cancer. The role of MUC16 in tumor progression and metastasis occurs through interaction with oncogenic modulators. For instance, it is understood that aberrant expression of MUC16 in ovarian cancer cells facilitates peritoneal metastasis through interactions with mesothelin (tumor differentiation factor) and through immunosuppressive functions by blocking natural killer cell-mediated cytotoxicity, while overexpression of MUC16 increases breast cancer cell proliferation via stimulation of Janus kinase 2 (JAK2). It is also understood that MUC16 is upregulated in pancreatic cancers, and expression is increased in liver metastases—although expression of MUC16 was not detected in pancreatic intraepithelial neoplasia (PanIN) nor in normal pancreas, suggesting that expression of MUC16 may occur later in disease progression.

The administration of mono-immunotherapy, in the form of MUC16-specific murine monoclonal antibody oregovomab (mAb-M43.13) following front-line therapy with chemotherapy failed to improves clinical outcome in advanced ovarian cancer (Berek et al. J Clin Onc 27:418-425, 2009). Furthermore a study of chemo-immunotherapy by Braly et al. (J Immunother 2009; 32:54-65) showed that simultaneous administration of oregovomab immunotherapy with the standard carboplatin-paclitaxel chemotherapy resulted in more vigorous immune response to the immunization than following chemotherapy. However, this study did not comprise a treatment group without oregovomab immunotherapy. Also, this study did not assess what the ideal duration of immunization would be for a beneficial treatment. Therefore, the benefits of combining immunotherapy with chemotherapy remained unclear.

Therefore, there is a need for novel method for use of therapeutic monoclonal antibodies with immune adjuvants.

SUMMARY

According to an embodiment, there is provided a method of inhibiting cancer tumor growth in a patient in need thereof, comprising:
at least a first treatment comprising steps a) and b):
a) administering to the patient an immune adjuvant in combination with a therapeutic monoclonal antibody specific for a tumor associated antigen; and
b) administering to the patient the immune adjuvant; and
a final treatment consisting of administering to the patient the therapeutic monoclonal antibody specific for a tumor associated antigen,
wherein time between step a) and step b) may be a time sufficient for treatment of the patient with the immune adjuvant, and wherein time between the step b) and the final treatment may be from about 10 to about 14 weeks.

The method may further comprise a second treatment comprising step a) and step b), with a time sufficient for treatment of the patient with the immune adjuvant between the step b) of the first treatment and step a) of the second treatment.

The method may further comprise a third treatment comprising step a) and step b), with a time sufficient for treatment of the patient with the immune adjuvant between the step b) of the second treatment and step a) of the third treatment.

According to another embodiment, there is provided a method of inhibiting cancer tumor growth in a patient in need thereof, comprising:
a first, second and third treatment comprising steps a) and b):
a) administering to the patient a therapeutic monoclonal antibody specific for an tumor associated antigen in combination with an immune adjuvant; and
b) administering to the patient the immune adjuvant; and
a final treatment consisting of administering to the patient the therapeutic monoclonal antibody specific for a tumor associated antigen,
wherein time between step a) and step b) may be from a time sufficient for treatment of the patient with the immune adjuvant, wherein time between step b) of the first treatment and step a) of the second treatment, and step b) of the second treatment and step a) of the third treatment may be a time sufficient for treatment of the patient with the immune adjuvant, and wherein time between the at least one treatment and the final treatment may be from about 10 to about 14 weeks.

The immune adjuvant may be a chemotherapeutic agent, an immunostimulatory compound, an immune homeostatic checkpoint inhibitor, or a combination thereof.

The therapeutic monoclonal antibody specific for a tumor associated antigen may be an antibody specific to CA125. The antibody specific to CA125 may be mAb-B43.13 (oregovomab).

The chemotherapeutic agent may be a platinum-based chemotherapy, TAXOL®, doxorubicin, topotecan, a poly (adenosine diphosphate-ribose) polymerase (PARP) inhibitor, or combinations thereof.

The platinum-based chemotherapy comprises cisplatin, carboplatin, oxaliplatin, nedaplatin, triplatin tetranitrate, phenanthriplatin, picoplatin, satraplatin, and combinations thereof.

The immunostimulatory compound may be a TLR3 agonist, a TLR4 agonist, or combinations thereof.

The TLR3 agonist may be polyiC, polyICLC (Hiltonol®).

The chemotherapeutic agent may be a combination of carboplatin and TAXOL®.

The therapeutic monoclonal antibody specific for a tumor associated antigen may be mAb-B43.13 (oregovomab), and the chemotherapeutic agent is a combination of carboplatin and TAXOL®.

The immune homeostatic checkpoint inhibitor may be an anti-PDL-1 antibody, an anti-CTLA-4 antibody, and anti-PD-1 antibody, or combinations thereof.

The anti-PDL-1 antibody may be selected from the group consisting of B7-H1 antibody, BMS-936559 antibody, MPDL3280A (atezolizumab) antibody, MEDI-4736 antibody, MSB0010718C antibody or combinations thereof.

The anti-CTLA-4 antibody may be selected from the group consisting of ipilimumab or tremelimumab or combinations thereof.

The anti-PD-1 antibody may be selected from the group consisting of Nivolumab antibody, pembrolizumab antibody, pidilizumab antibody or combinations thereof, and AMP-224.

The a poly(adenosine diphosphate-ribose) polymerase (PARP) inhibitor is selected from the group consisting of olaparib, niraparib, rucaparib, talazoparib, veliparib, CEP 9722, E7016, and BGB-290, or combinations thereof.

The cancer may be ovarian cancer.

According to another embodiment, there is provided an immune adjuvant and a therapeutic monoclonal antibody specific for a tumor associated antigen for use in inhibiting tumor cancer growth in a patient, wherein the immune adjuvant and therapeutic monoclonal antibody specific for a tumor associated antigen are administered according to:
  at least one sequential use of (a) followed by (b):
  (a) the immune adjuvant and the therapeutic monoclonal antibody specific for a tumor associated antigen, administered together to the patient;
  (b) the immune adjuvant, administered to the patient; and
  a final use consisting of the therapeutic monoclonal antibody specific for a tumor associated antigen, administered to the patient,
wherein time between (a) and (b) is a time sufficient for treatment of the patient with the immune adjuvant, and wherein time between the (b) and the final use is from about 10 to about 14 weeks.

The immune adjuvant and a therapeutic monoclonal antibody specific for a tumor associated antigen may further comprise another (a second) sequential use of (a) followed by (b) according to the present invention.

The immune adjuvant and a therapeutic monoclonal antibody specific for a tumor associated antigen may further comprise another (a third) sequential use of (a) followed by (b) according to the present invention.

The immune adjuvant and a therapeutic monoclonal antibody specific for a tumor associated antigen according to the present invention may comprise:
  a first, second and third sequential use of (a) followed by (b):
  (a) the immune adjuvant and the therapeutic monoclonal antibody specific for a tumor associated antigen, administered together to the patient;
  (b) the immune adjuvant, administered to the patient; and
  a final use consisting of the therapeutic monoclonal antibody specific for a tumor associated antigen administered to the patient,
wherein time between (a) and (b) is from a time sufficient for treatment of the patient with the immune adjuvant,
wherein time between (b) of the first sequential use and (a) of the second sequential use, and (b) of the second sequential use and (a) of the third sequential use is a time sufficient for treatment of the patient with the immune adjuvant, and
wherein time between the third sequential use and the final use is from about 10 to about 14 weeks.

The immune adjuvant may be a chemotherapeutic agent, an immunostimulatory compound, an immune homeostatic checkpoint inhibitor, or a combination thereof.

The therapeutic monoclonal antibody specific for a tumor associated antigen may be an antibody specific to CA125.

The antibody specific to CA125 may be mAb-B43.13 (oregovomab).

The chemotherapeutic agent may be a platinum-based chemotherapy, TAXOL®, doxorubicin, topotecan, a poly (adenosine diphosphate-ribose) polymerase (PARP) inhibitor, or combinations thereof.

The platinum-based chemotherapy may comprise cisplatin, carboplatin, oxaliplatin, nedaplatin, triplatin tetranitrate, phenanthriplatin, picoplatin, satraplatin, and combinations thereof.

The immunostimulatory compound may be a TLR3 agonist, a TLR4 agonist, or combinations thereof, preferably, the TLR3 agonist may be polyiC, polyICLC (Hiltonol®).

The chemotherapeutic agent may be a combination of carboplatin and TAXOL®.

The therapeutic monoclonal antibody specific for a tumor associated antigen may be mAb-B43.13 (oregovomab), and the chemotherapeutic agent may be a combination of carboplatin and TAXOL®.

The immune homeostatic checkpoint inhibitor may be an anti-PDL-1 antibody, an anti-CTLA-4 antibody, and anti-PD-1 antibody, or combinations thereof.

The anti-PDL-1 antibody may be selected from the group consisting of B7-H1 antibody, BMS-936559 antibody, MPDL3280A (atezolizumab) antibody, MEDI-4736 antibody, MSB0010718C antibody or combinations thereof; the anti-CTLA-4 antibody may be selected from the group consisting of ipilimumab or tremelimumab or combinations thereof, and the anti-PD-1 antibody may be selected from the group consisting of Nivolumab antibody, pembrolizumab antibody, pidilizumab antibody or combinations thereof, and AMP-224.

The a poly(adenosine diphosphate-ribose) polymerase (PARP) inhibitor is selected from the group consisting of olaparib, niraparib, rucaparib, talazoparib, veliparib, CEP 9722, E7016, and BGB-290, or combinations thereof.

The cancer may be ovarian cancer.

According to another embodiment, there is provided a therapeutic agent for use in inhibiting tumor cancer growth in a patient, comprising an immune adjuvant and a therapeutic monoclonal antibody specific for a tumor associated antigen, wherein the therapeutic agent may be administered according to:
- at least one sequential use of (a) followed by (b):
  - (a) a combination of the immune adjuvant and the therapeutic monoclonal antibody specific for a tumor associated antigen;
  - (b) the immune adjuvant; and
  - a final use consisting of the therapeutic monoclonal antibody specific for a tumor associated antigen, wherein time between (a) and (b) is a time sufficient for treatment of the patient with the immune adjuvant, and wherein time between the (b) and the final use is from about 10 to about 14 weeks.

The therapeutic agent may further comprise another (a second) sequential use of (a) followed by (b) according to the present invention.

The therapeutic agent may further comprise another (a third) sequential use of (a) followed by (b) according to the present invention.

The therapeutic agent according to the present invention, may comprise:
- a first, second and third sequential use of (a) followed by (b):
  - (a) the immune adjuvant and the therapeutic monoclonal antibody specific for a tumor associated antigen;
  - (b) the immune adjuvant; and
  - a final use consisting the therapeutic monoclonal antibody specific for a tumor associated antigen, wherein time between (a) and (b) is from a time sufficient for treatment of the patient with the immune adjuvant, wherein time between (b) of the first use and (a) of the second use, and (b) of the second use and (a) of the third use is a time sufficient for treatment of the patient with the immune adjuvant, and wherein time between the third sequential use and the final use is from about 10 to about 14 weeks.

The immune adjuvant may be a chemotherapeutic agent, an immunostimulatory compound, an immune homeostatic checkpoint inhibitor, or a combination thereof.

The therapeutic monoclonal antibody specific for a tumor associated antigen may be an antibody specific to CA125.

The antibody specific to CA125 may be mAb-B43.13 (oregovomab).

The chemotherapeutic agent may be a platinum-based chemotherapy, TAXOL®, doxorubicin, topotecan, a poly(adenosine diphosphate-ribose) polymerase (PARP) inhibitor, or combinations thereof.

The platinum-based chemotherapy comprises cisplatin, carboplatin, oxaliplatin, nedaplatin, triplatin tetranitrate, phenanthriplatin, picoplatin, satraplatin, and combinations thereof.

The chemotherapeutic agent may be a combination of carboplatin and TAXOL®.

The therapeutic monoclonal antibody specific for a tumor associated antigen may be mAb-B43.13 (oregovomab), and the chemotherapeutic agent may be a combination of carboplatin and TAXOL®.

The immunostimulatory compound may be a TLR3 agonist, a TLR4 agonist, or combinations thereof.

The TLR3 agonist may be polyiC, polyICLC (Hiltonol®).

The immune homeostatic checkpoint inhibitor may be an anti-PDL-1 antibody, an anti-CTLA-4 antibody, and anti-PD-1 antibody, or combinations thereof.

The anti-PDL-1 antibody may be selected from the group consisting of B7-H1 antibody, BMS-936559 antibody, MPDL3280A (atezolizumab) antibody, MEDI-4736 antibody, MSB0010718C antibody or combinations thereof.

The anti-CTLA-4 antibody may be selected from the group consisting of ipilimumab or tremelimumab or combinations thereof.

The anti-PD-1 antibody may be selected from the group consisting of Nivolumab antibody, pembrolizumab antibody, pidilizumab antibody or combinations thereof, and AMP-224.

The a poly(adenosine diphosphate-ribose) polymerase (PARP) inhibitor is selected from the group consisting of olaparib, niraparib, rucaparib, talazoparib, veliparib, CEP 9722, E7016, and BGB-290, or combinations thereof.

The cancer may be ovarian cancer.

The following terms are defined below.

The terms "administration of" and/or "administering a" is intended to mean providing an antibody according to the present invention with or without additional compound(s) to a subject in need of treatment.

The term "composition" intended to mean a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s) and the inert ingredient(s) that make up the pharmaceutically acceptable carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing an antibody according to the present invention and a pharmaceutically acceptable carrier. By "pharmaceutically acceptable" it is meant the carrier, diluent or excipient must be compatible with the other ingredients of the formulation and not deleterious to the recipient thereof.

The term "immune adjuvant" is intended to mean a component that potentiates the immune responses to an antigen and/or modulates it towards the desired immune responses. It is a substance that acts to accelerate, prolong, or enhance antigen-specific immune responses when used in combination with specific antigens. In the context of the present invention, this includes chemotherapeutic agents such as for example platinum-based chemotherapy, TAXOL®, doxorubicin, topotecan, a poly(adenosine diphosphate-ribose) polymerase (PARP) inhibitor, or combinations thereof, immunostimulatory compounds such as for example TLR3 agonist and TLR4 agonist, and their combinations, immune homeostatic checkpoint inhibitor such as for example anti-PDL-1 antibody, an anti-CTLA-4 antibody, and anti-PD-1 antibody, and their combinations; or a combination thereof. In embodiments, the immune adjuvant property(ies) of the immune adjuvant may be in addition to other therapeutic properties, such as for example cytotoxicity. That is to say, without wishing to be bound by theory, the immune adjuvants as described herein may not only act as an immune adjuvant, but may have other therapeutic properties for which, for example, it may be used in therapy. Such therapy may be, for example, as standard of care therapy for a given cancer.

The term "chemotherapy regimen" is intended to mean combination of several chemotherapeutic agents. The rationale behind such chemotherapy regimen is that different chemotherapy drugs work through different cytotoxic mechanisms, and that the results of using multiple drugs will be synergistic to some extent. Because they have different dose-limiting adverse effects, they can be given together at full doses in chemotherapy regimens. Chemotherapy regimen may include induction and maintenance regimen.

The term "induction regimen" is intended to mean a chemotherapy regimen used for the initial treatment of a disease.

The term "maintenance regimen" is intended to mean the ongoing use of chemotherapy to reduce the chances of a cancer recurring or to prevent an existing cancer from continuing to grow.

In some embodiments, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the antibody or fragment thereof, preferably in purified form, together with a suitable amount of carrier so as to provide the form for proper administration to the patient. The formulation should suit the mode of administration.

The terms "inhibit", "inhibition" or "inhibiting" as used herein in the context of the invention means to slow, hinder, restrain reduce or prevent. For example, "inhibiting growth" of a tumor cell as that term is used herein means to slow, hinder, restrain, reduce or prevent the tumor cell from growing.

The term "administering" as used herein refers to any action that results in exposing or contacting a composition containing a therapeutic monoclonal antibody specific for a tumor associated antigen in combination with at least one immunostimulatory compound, and at least one immune homeostatic checkpoint inhibitor, according to the invention with a pre-determined cell, cells, or tissue, typically mammalian. As used herein, administering may be conducted in vivo, in vitro, or ex vivo. For example, a composition may be administered by injection or through an endoscope. Administering also includes the direct application to cells of a composition according to the present invention. For example, during the course of surgery, tumor cells may be exposed. In accordance with an embodiment of the invention, these exposed cells (or tumors) may be exposed directly to a composition of the present invention, e.g., by washing or irrigating the surgical site and/or the cells, or by direct intra-tumoral injection of the therapeutic monoclonal antibody specific for a tumor associated antigen in combination with at least one immunostimulatory compound, and at least one immune homeostatic checkpoint inhibitor individually or in a mixture.

The term "epitope" is intended to mean the portion of an antigen capable of being recognized by and bound by an antibody at one or more of the antibody's binding regions. Epitopes generally comprise chemically active surface groupings of molecules such as amino acids or sugar side chains and have specific three dimensional structure characteristics as well as specific charge characteristics. In one embodiment, an epitope of an antigen is a repetitive epitope. In one embodiment an epitope of an antigen is a non-repetitive epitope.

The term "subject" as used herein, is a human patient or other animal such as another mammal with functional mast cells, basophils, neutrophils, eosinophils, monocytes, macrophages, dendritic cells, and Langerhans cells. In humans, the appropriate cells express the high affinity receptor for IgG for the administered IgG antibody of the invention, as well as IgE (FcεRI) for the administered IgE antibody of the invention.

As used herein, a reduction in growth kinetics, or complete elimination of, a cancer tumor or a metastasized cell or tumor as used herein is defined to mean that which is as understood in the art. For example, a reduction in growth kinetics means a reduction in the exponential growth, specific growth rate, or doubling time of a primary solid tumor, metastasized cell, or metastasized tumor relative to the exponential growth, specific growth rate, or doubling time normally observed in vivo or in vitro for a given tumor type. Complete elimination of a tumor is the absence of tumor presence, either by symptoms, physical exam, or radiographic imaging, in the presence of the therapeutic monoclonal antibody specific for a tumor associated antigen in combination with at least one immunostimulatory compound, and at least one immune homeostatic checkpoint inhibitor, where a tumor was previously seen to be present by these detection methodologies.

The term "tumor-associated antigen" (TAA) as used herein can be any type of cancer antigen that may be associated with a tumor as is known in the art and includes antigens found on the cell surface, including tumor cells, as well as soluble cancer antigens. Several cell surface antigens on tumors and normal cells have soluble counterparts. Such antigens include, but are not limited to those found on cancer-associated fibroblasts (CAFs), tumor endothelial cells (TEC) and tumor-associated macrophages (TAM). Examples of cancer-associated fibroblasts (CAFs) target antigens include but are not limited to: carbonic anhydrase IX (CAIX); fibroblast activation protein alpha (FAPα); and matrix metalloproteinases (MMPs) including MMP-2 and MMP-9. Examples of Tumor endothelial cell (TECs) target antigens include, but are not limited to vascular endothelial growth factor (VEGF) including VEGFR-1, 2, and 3; CD-105 (endoglin), tumor endothelia markers (TEMs) including TEM1 and TEM8; MMP-2; Survivin; and prostate-specific membrane antigen (PMSA). Examples of tumor associated macrophage antigens include, but are not limited to: CD105; MMP-9; VEGFR-1, 2, 3 and TEM8. According to some embodiments, the tumor associated antigen may be CA125, folate binding protein (FBP), HER2/neu, MUC1 or PSA.

The term "time sufficient for treatment" or "a time sufficient for treatment of the patient with the immune adjuvant" is intended to mean any period of time suitable to effect treatment with the immune adjuvant. In embodiments, that time period may be the time of a cycle used in standard to care for the immune adjuvant (e.g. chemotherapy). Examples of standard of care treatments may be found for example in Gynecologic Oncology Group Chemotherapy Procedures Manual, incorporated herein by reference. The length of chemotherapy treatment is determined by a variety of factors. These include the type of cancer, the extent of cancer, the types of drugs that are given, as well as the expected toxicities of the drugs and the amount of time necessary to recover from these toxicities. Many chemotherapy treatment schedules (often referred to as Standard of Care (SOC), including the type and length of chemotherapy treatment) have been determined through clinical trials that compared them and determined which had the most benefit and was most well tolerated. In general, chemotherapy treatment is given in cycles. This allows the cancer cells to be attacked at their most vulnerable times, and allows the body's normal cells time to recover from the damage. There are really three issues regarding the cycle time, duration of the cycle, frequency of the cycle, and how many cycles. Duration of the cycle: chemotherapy treatment may be a single drug or a combination of drugs. The drugs may all be given on a single day, several consecutive days, or continuously as an outpatient or as an inpatient. Treatment could last minutes, hours, or days, depending on the specific protocol. Frequency of the cycle: chemotherapy may repeat weekly, bi-weekly, or monthly. Usually, a cycle is defined in monthly intervals. For example, two bi-weekly chemotherapy sessions may be classified as one cycle. The number of cycles: In most cases, the number of cycles—or the length of chemotherapy from start to finish—has been determined by research and clinical trials. When cure is the treatment goal. Adjuvant chemotherapy (therapy after surgery has removed all visible cancer) may last 4-6 months. Adjuvant chemotherapy is common in cancers of the breast and colon. In cancers of the testis, Hodgkin and non-Hodgkin lymphoma, and leukemias, length of chemotherapy treatment may be up to a year. When there is visible disease, the length of chemotherapy treatment will depend upon the response of the disease to therapy. If the disease disappears completely, chemotherapy may continue for 1-2 cycles beyond this observation to maximize the chance of having attacked all microscopic disease. If the disease shrinks but does not disappear, chemotherapy will continue as long as it is tolerated and the disease does not grow. If the disease grows, the chemotherapy will be stopped. As patients experience toxicities and blood cell counts, the actual timing of the cycles is sometimes delayed according the necessities of each patient's circumstance. Depending on the health and wishes of the patient, either different drugs may be given to try to kill the cancer, or chemotherapy will be stopped and the goal changed to focus on patient comfort. In an embodiment, for example, the administration of the immune adjuvant therapy combining paclitaxel and carboplatin is often performed in cycles of about 21 days (3 weeks).

Before describing the present invention in detail, a number of terms will be defined. As used herein, the singular forms "a", "an", and "the" include plural referents unless the context clearly dictates otherwise.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

Figure 1:
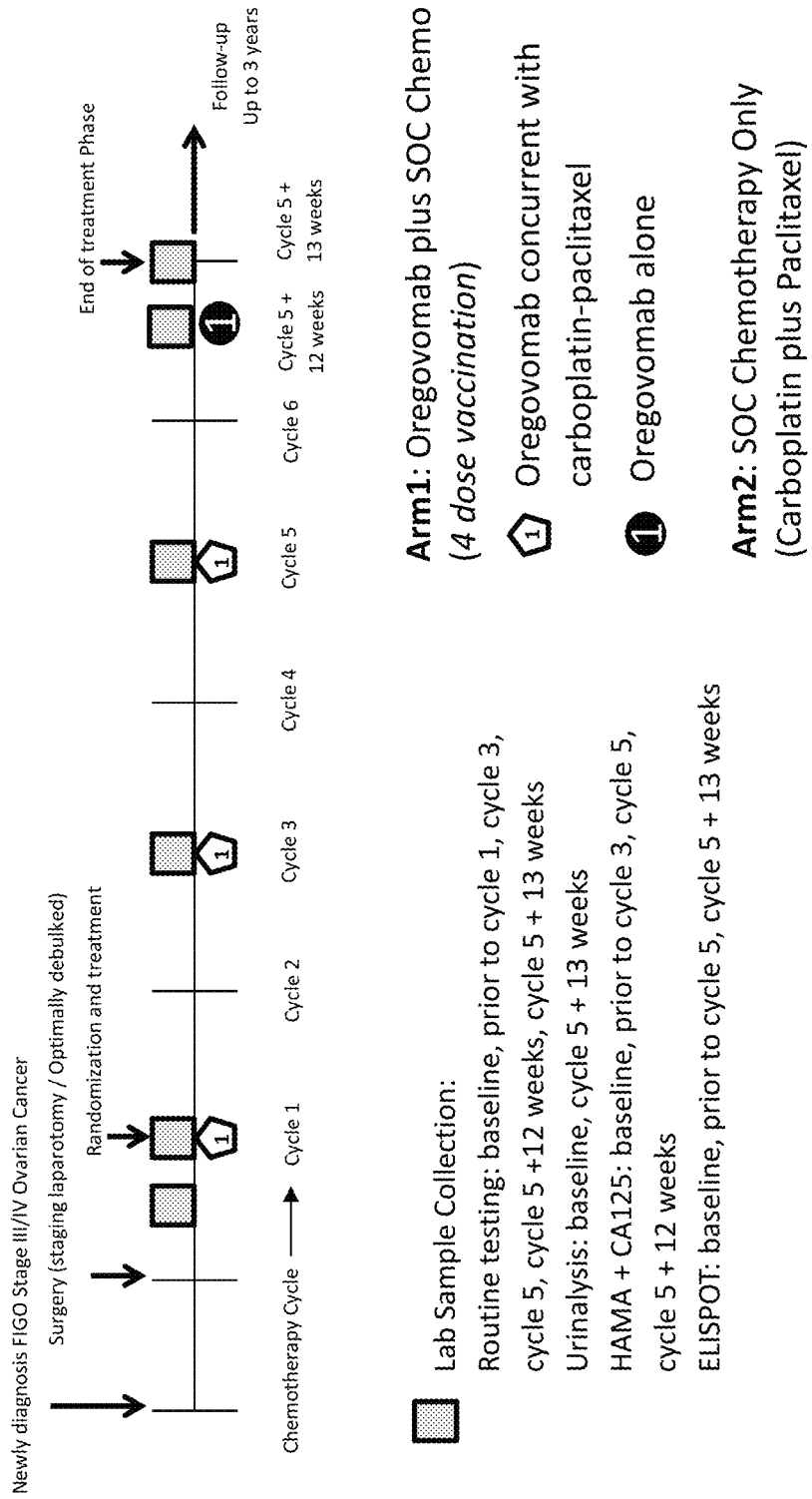
FIG. 1 illustrates a schematic of the Frontline Chemoimmunotherapy Randomized Phase II trial according to an embodiment of the present invention.
Figure 2:
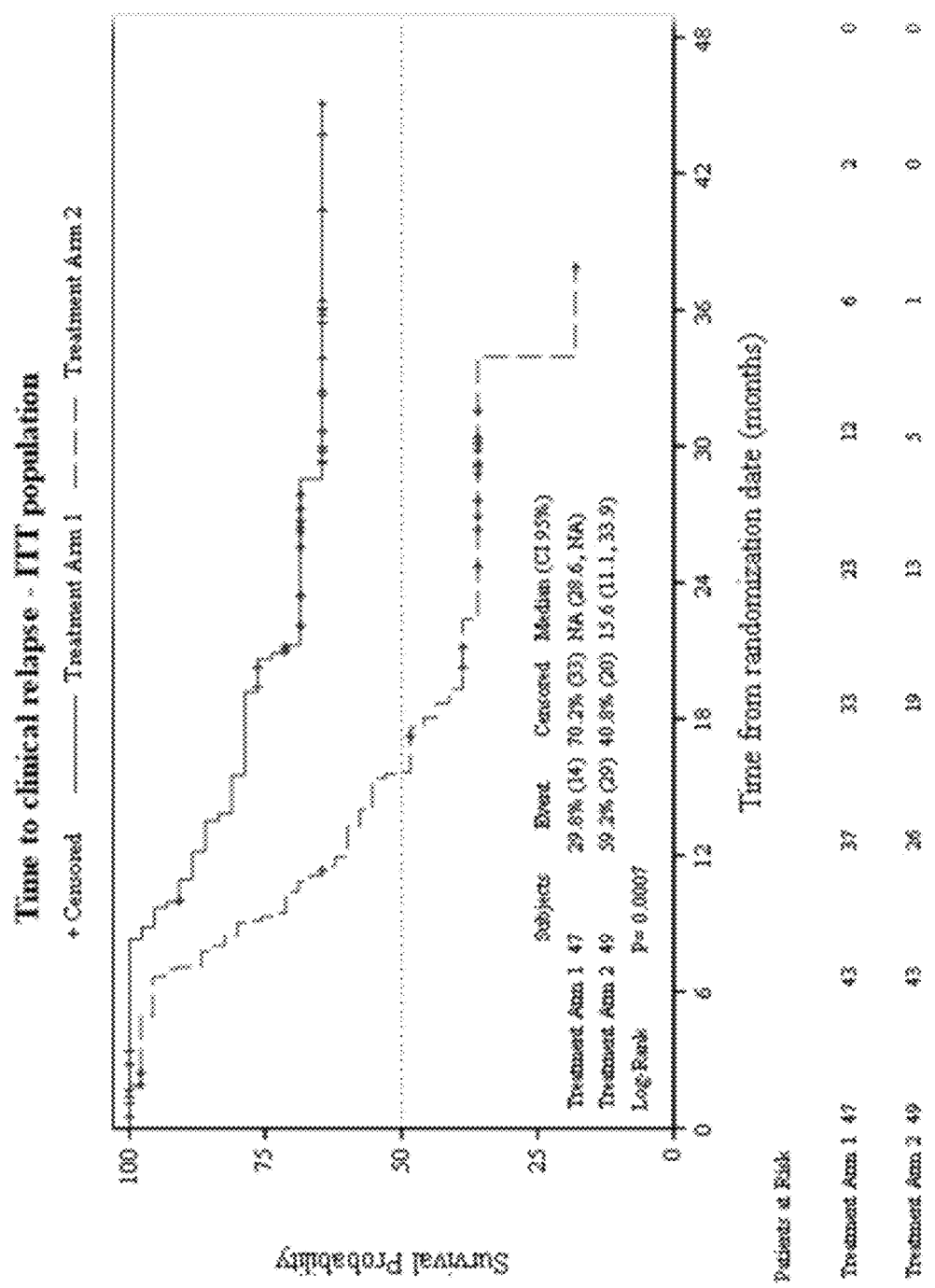
FIG. 2 illustrates the time to clinical relapse in the ITT population, for the CIT treatment arm (full line) and the SOC treatment arm (dash line)
Figure 3:
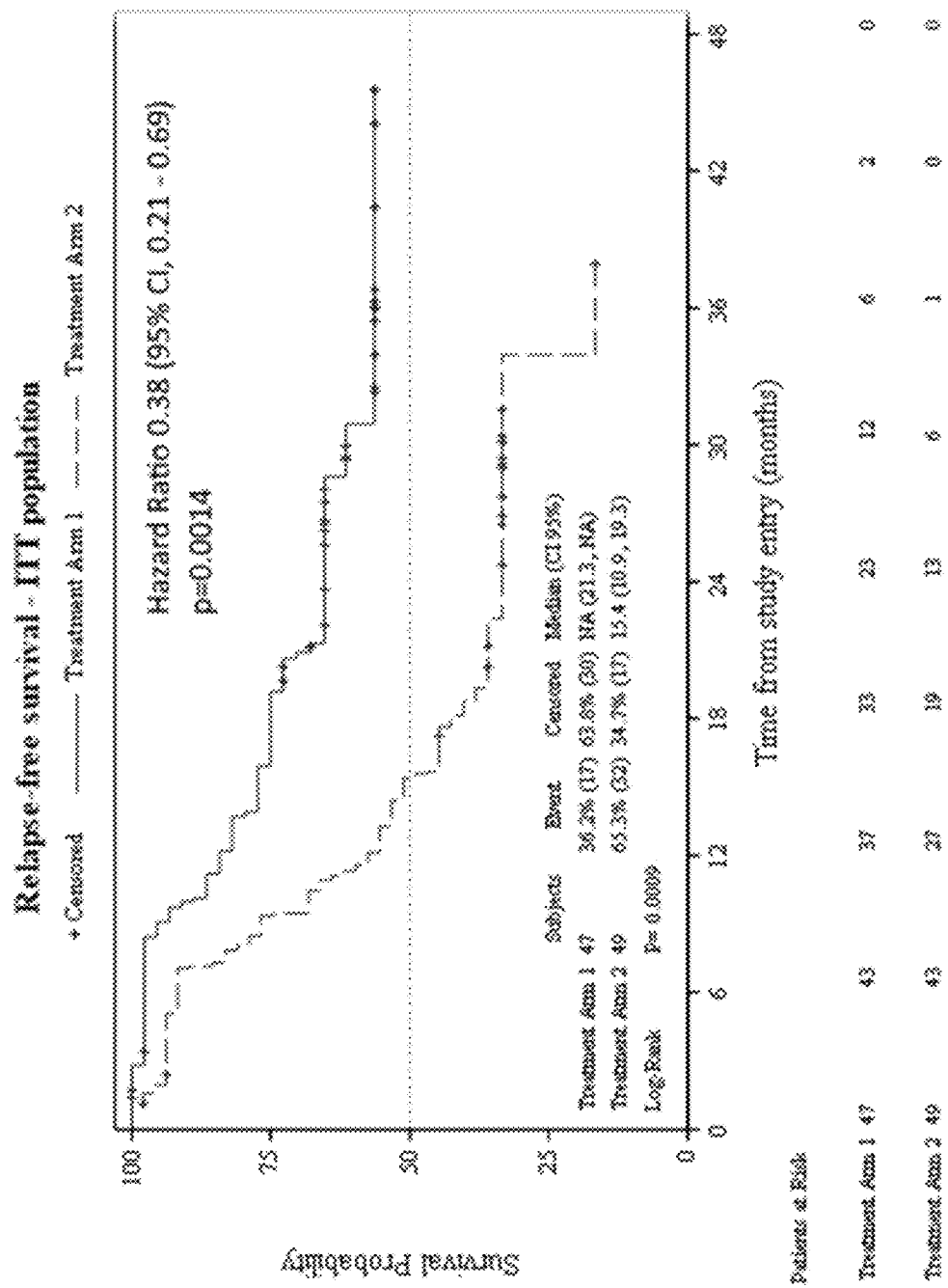
FIG. 3 illustrates relapse free survival in the ITT population, for the CIT treatment arm (full line) and the SOC treatment arm (dash line)
Figure 4:
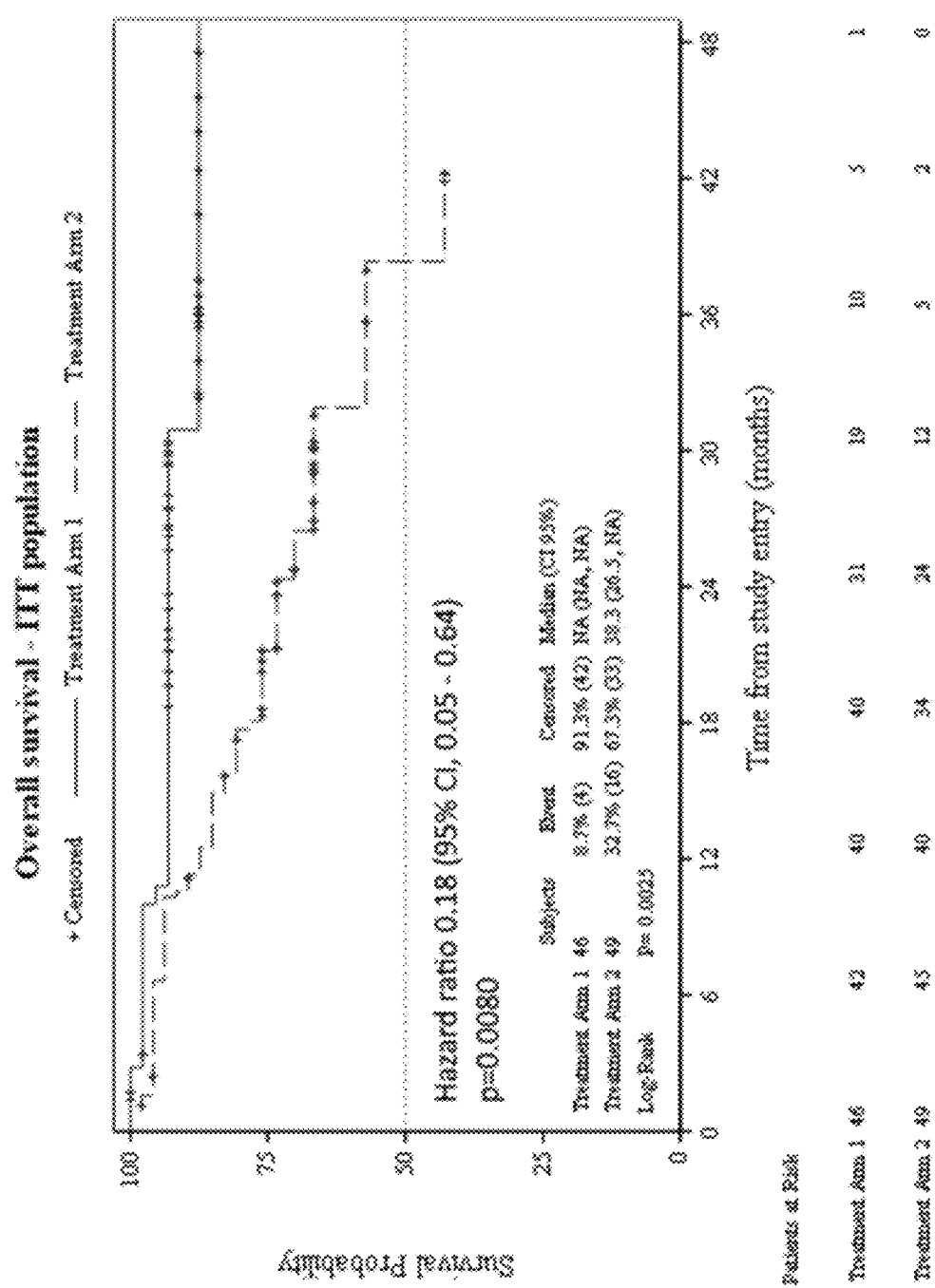
FIG. 4 illustrates overall survival in the ITT population, for the CIT treatment arm (full line) and the SOC treatment arm (dash line)
Figure 5:
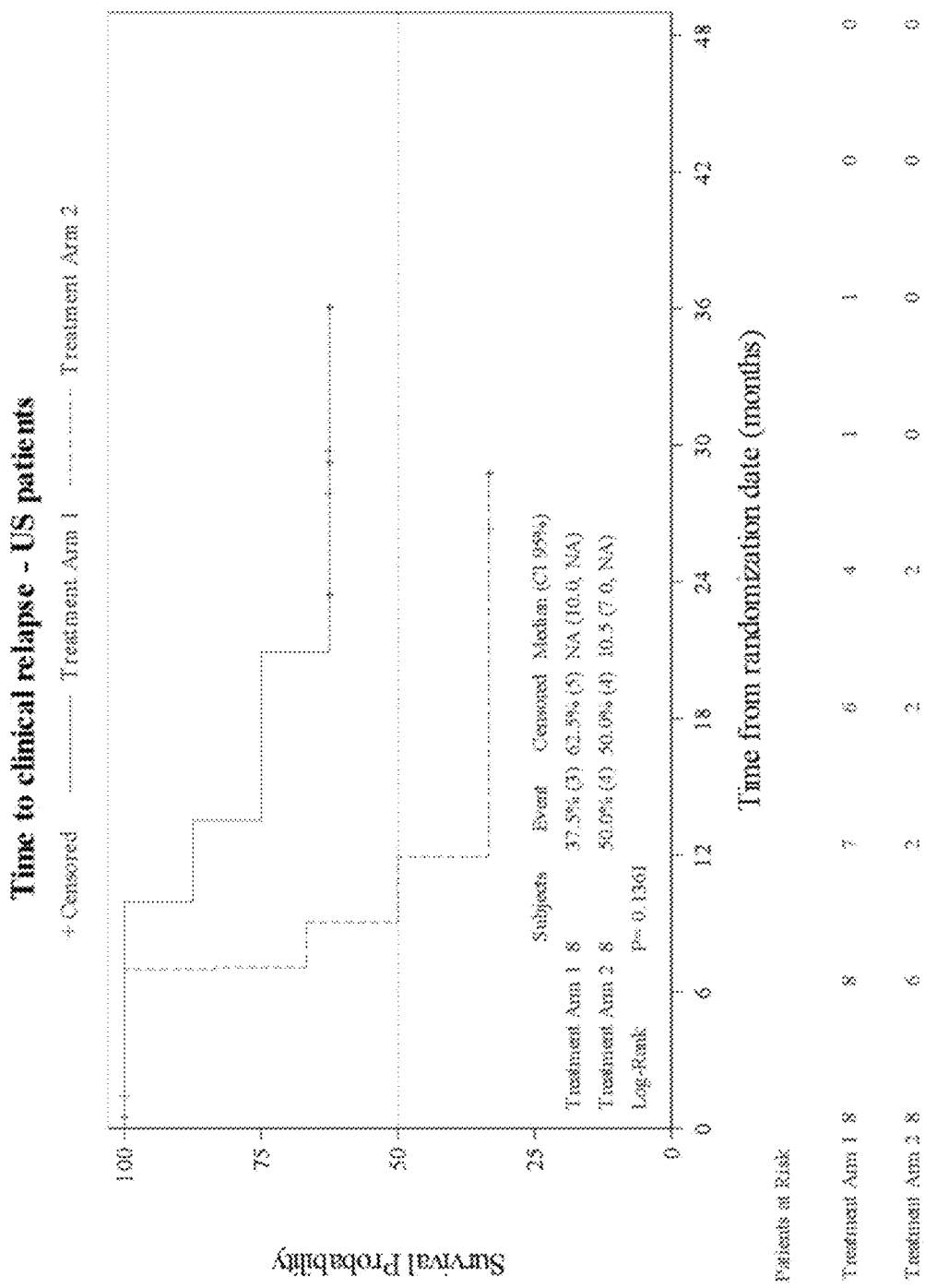
FIG. 5 illustrates the time to clinical relapse in the US patients part of the ITT population, for the CIT treatment arm (full line) and the SOC treatment arm (dash line)
Figure 6:
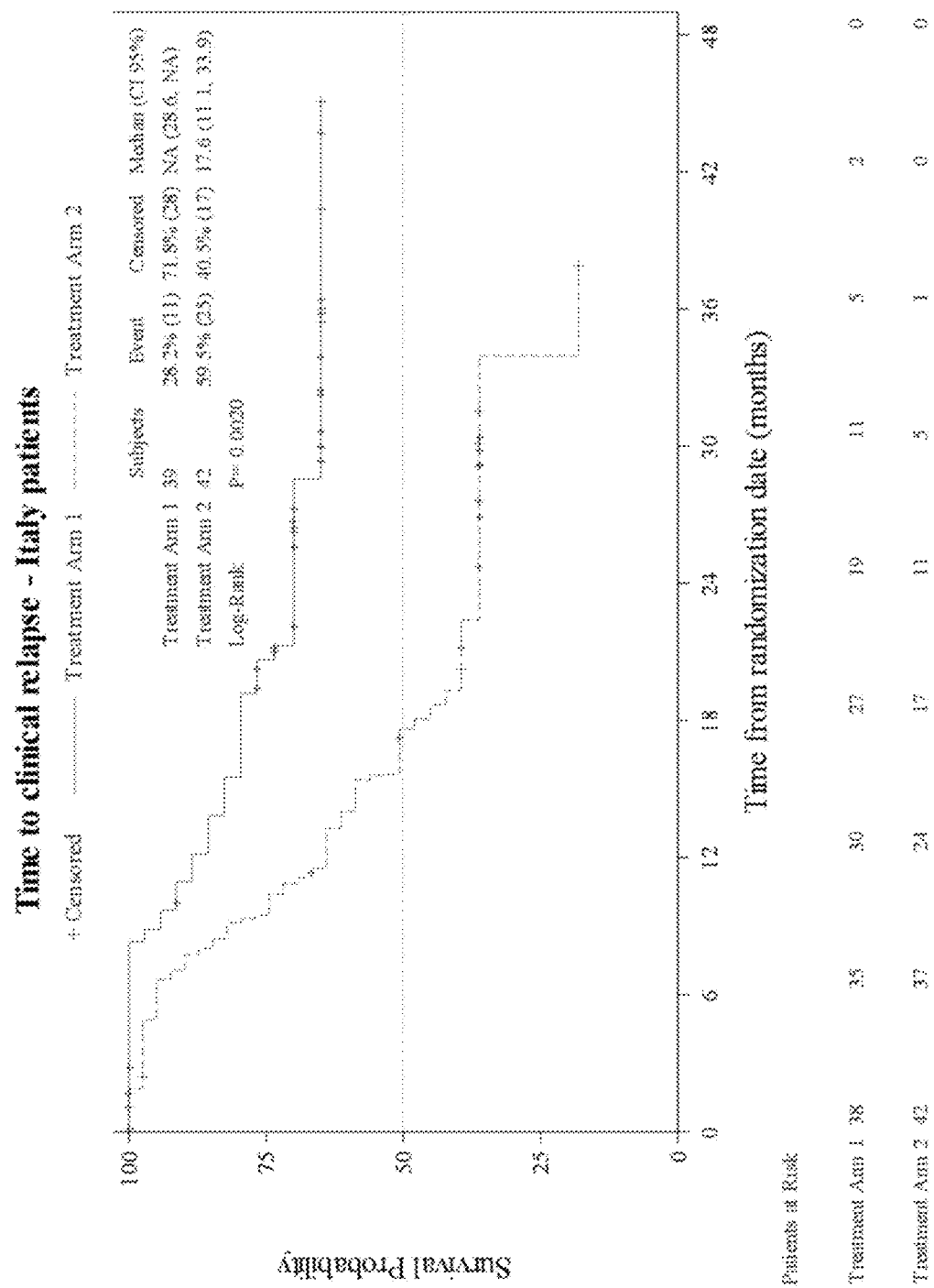
FIG. 6 illustrates the time to clinical relapse in the Italian patients of the ITT population, for the CIT treatment arm (full line) and the SOC treatment arm (dash line)
Figure 7:
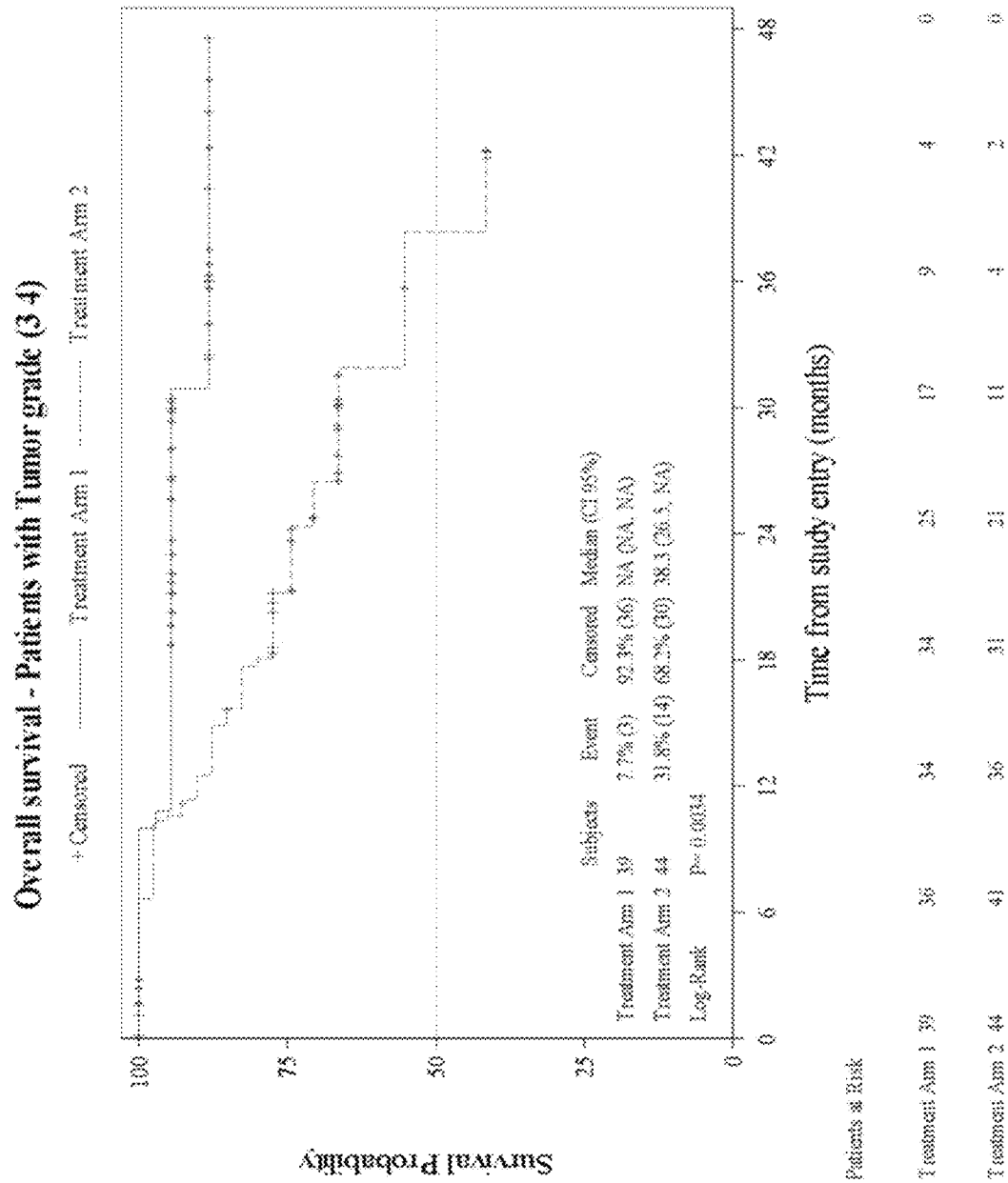
FIG. 7 illustrates overall survival of patients with Tumor grade 3 and 4 from the patients in the study group, for the CIT treatment arm (full line) and the SOC treatment arm (dash line)
Figure 8:
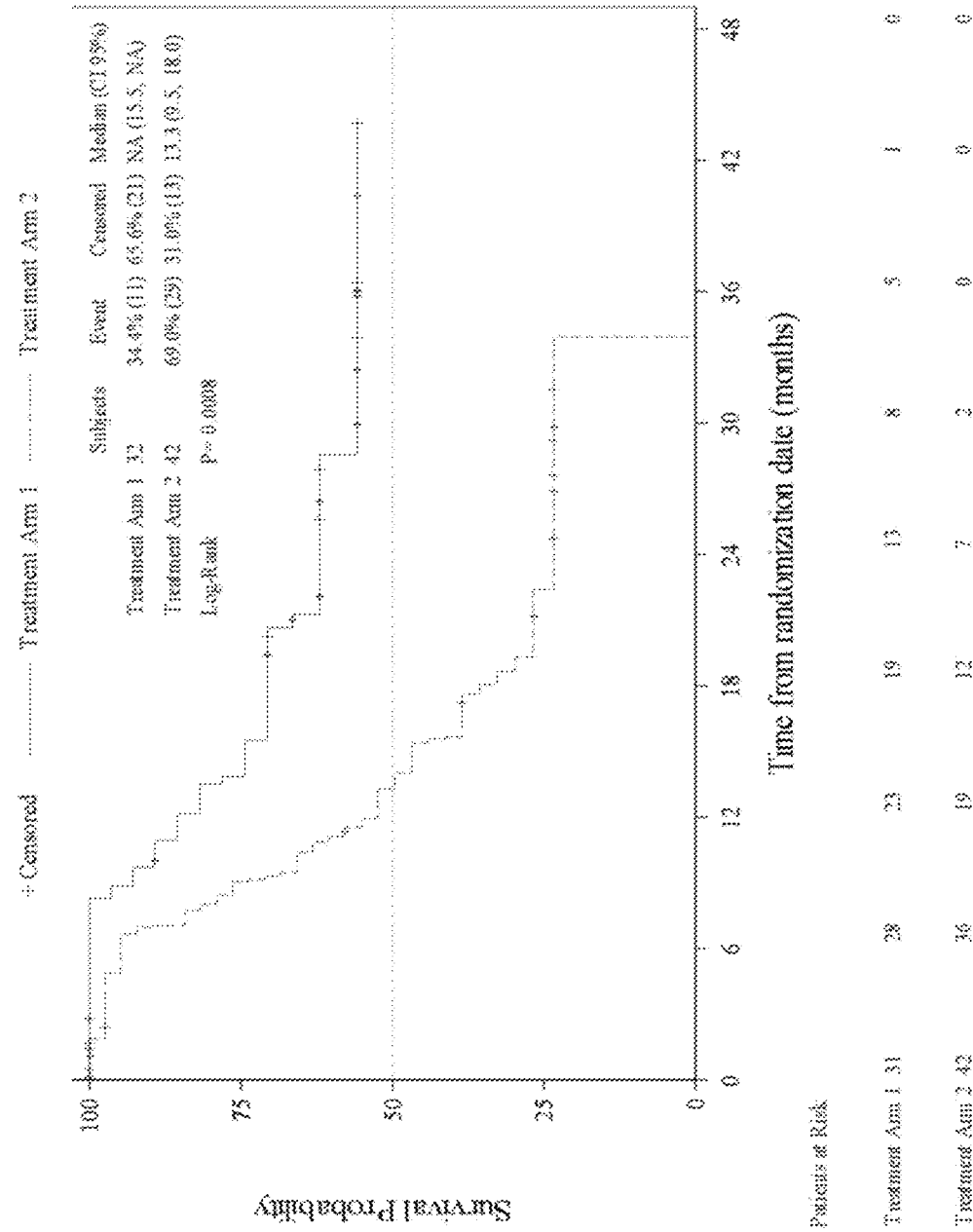
FIG. 8 illustrates time to clinical relapse of patients with FICO stage IIIC-IV from the patients in the study group, for the CIT treatment arm (full line) and the SOC treatment arm (dash line)
Figure 9:
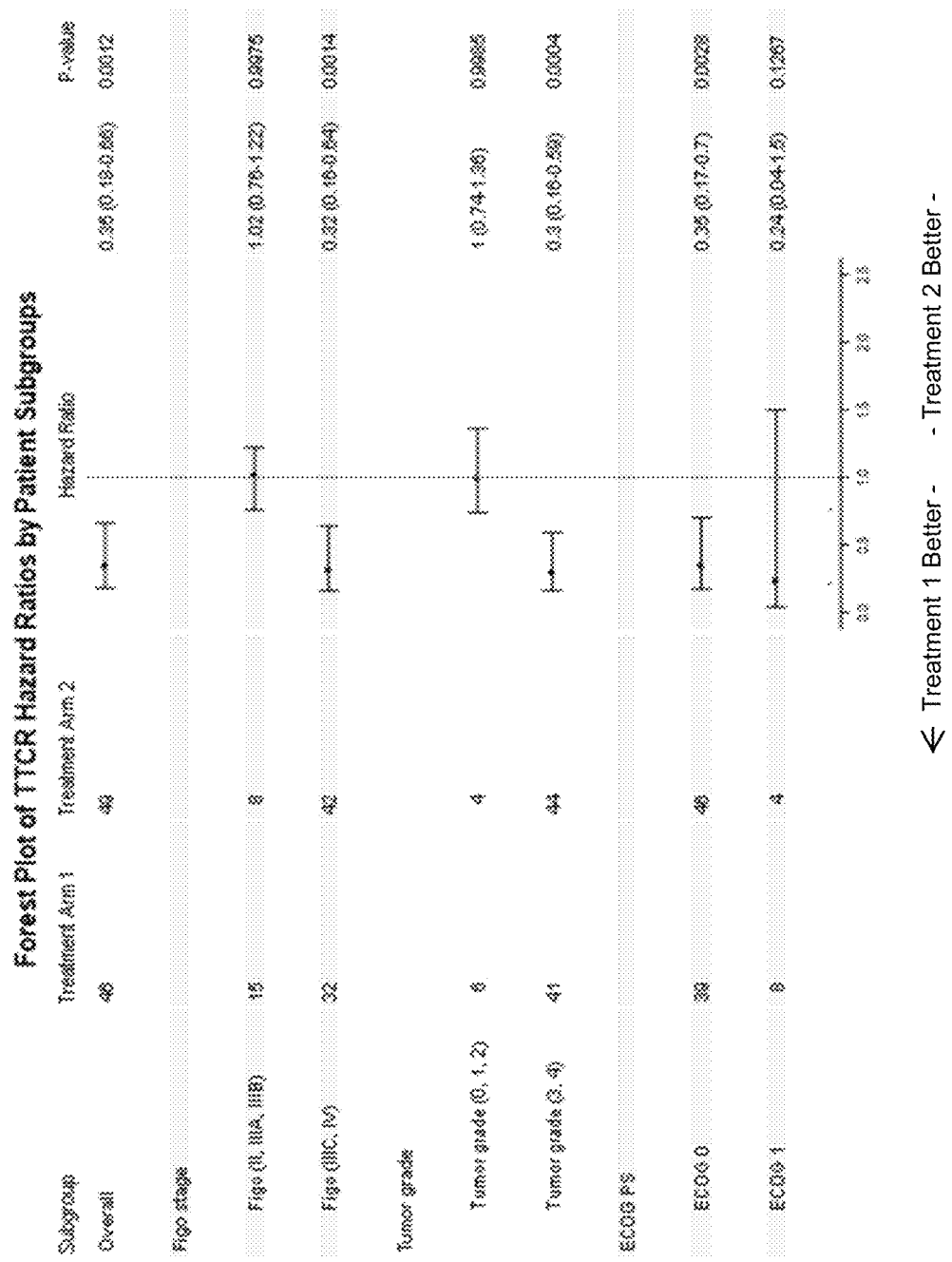
FIG. 9 illustrates a Forest plot of Time to clinical relapse (TTCR) hazard ratios by patient subgroups. Treatment 1=CIT; Treatment 2=SOC.
Figure 10:
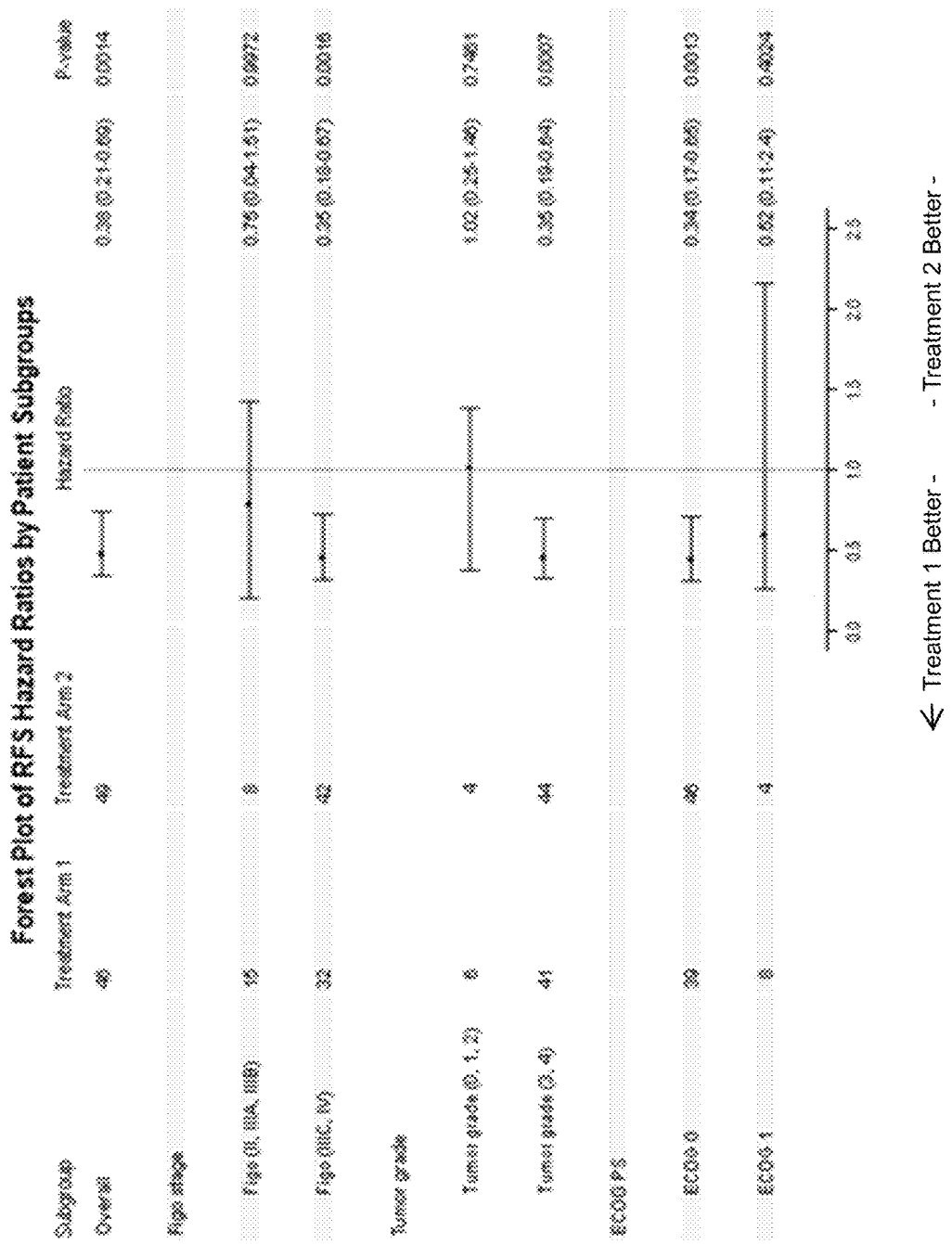
FIG. 10 illustrates a Forest plot of Relapse free survival (RFS) hazard ratios by patient subgroups. Treatment 1=CIT; Treatment 2=SOC.
Figure 11:
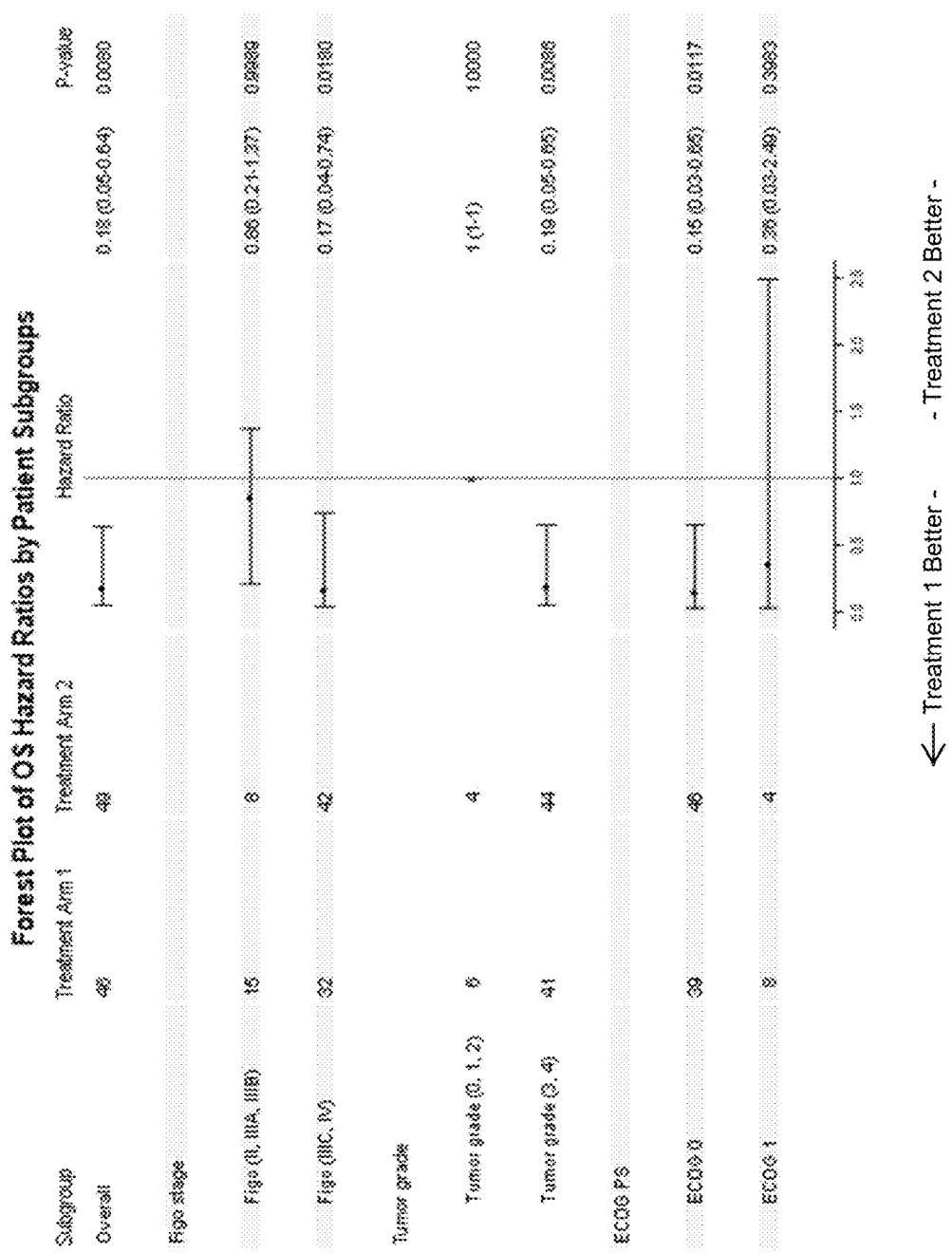
FIG. 11 illustrates a Forest plot of overall survival (OS) hazard ratios by patient subgroups. Treatment 1=CIT; Treatment 2=SOC.
Figure 12:
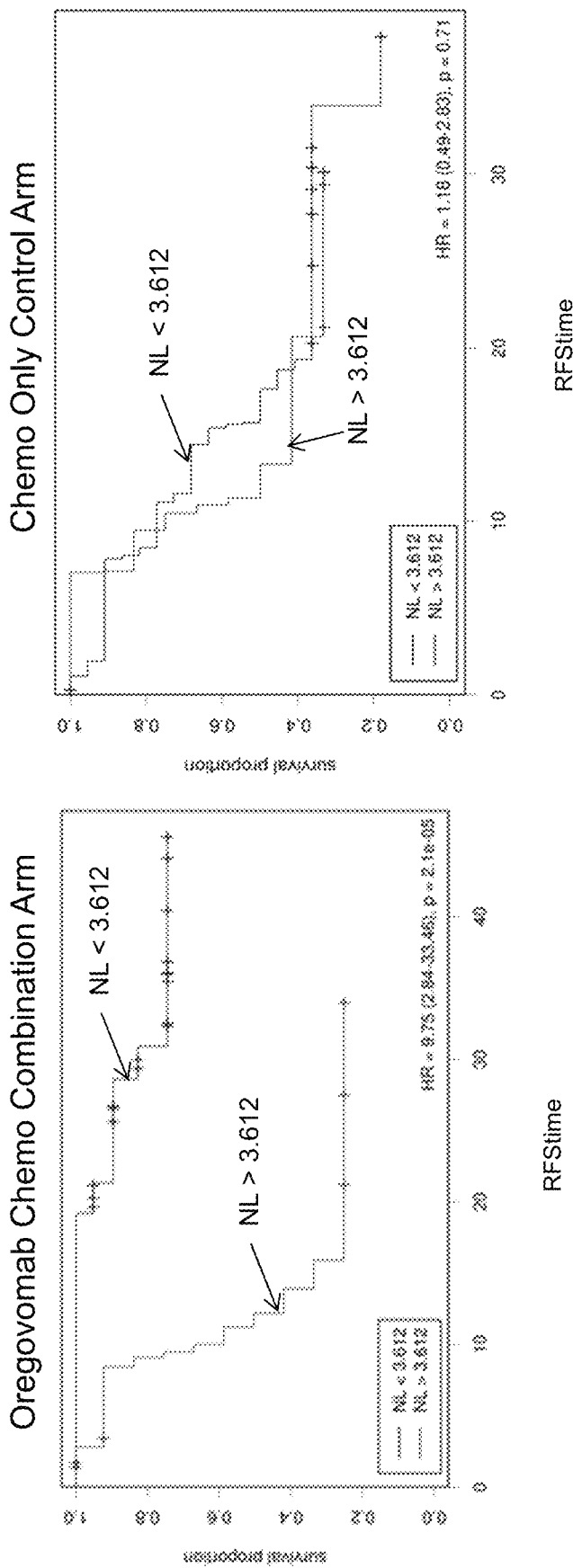
FIG. 12 illustrates the relapse free survival from the CIT group (left graph) and SOC group (right). The population from each group is segrated on the basis of the Neutrophil/lymphocyte ratio (NLR) at baseline and patients' clinical outcome in terms of RFS using a cut-off value of 3.612 for patients.

In embodiments there are disclosed a method of inhibiting cancer tumor growth in a patient in need thereof, comprising:
at least a first treatment comprising steps a) and b):
a) administering to the patient an immune adjuvant in combination with a therapeutic monoclonal antibody specific for a tumor associated antigen; and
b) administering to the patient the immune adjuvant; and
a final treatment consisting of administering to the patient the therapeutic monoclonal antibody specific for a tumor associated antigen,
wherein time between step a) and step b) is a time sufficient for treatment of the patient with the immune adjuvant, and wherein time between the step b) and the final treatment is from about 10 to about 14 weeks.

According to an embodiment, the method may further comprise a second treatment comprising steps a) and b), with a time sufficient for treatment of the patient with the immune adjuvant between step b) of the first treatment and step a) of the second treatment. In a preferred embodiment, the method further comprises a third treatment comprising steps a) and b), with a time sufficient for treatment of the patient with the immune adjuvant between step b) of the second treatment and step a) of the third treatment.

According to another embodiment, there is disclosed a method of inhibiting cancer tumor growth in a patient in need thereof, comprising:
a first, second and third treatment comprising steps a) and b):
a) administering to the patient an immune adjuvant in combination with a therapeutic monoclonal antibody specific for an tumor associated antigen; and
b) administering to the patient the immune adjuvant; and
a final treatment consisting of administering the therapeutic monoclonal antibody specific for a tumor associated antigen,
wherein time between step a) and step b) is a time sufficient for treatment of the patient with the immune adjuvant,
wherein time between step b) of the first treatment and step a) of the second treatment, and step b) of the second treatment and step a) of the third treatment is a time sufficient for treatment of the patient with the immune adjuvant, and wherein time between the at least one treatment and the final treatment is from about 10 to about 14 weeks.

In embodiments of the present invention, the term "in combination" is intended to mean that the therapeutic monoclonal antibody specific for an tumor associated antigen and the immune adjuvant are administered during the same treatment or treatment cycle. This includes administration conditions where the immune adjuvant is administered first, followed by administration of the therapeutic monoclonal antibody specific for an tumor associated antigen. This also includes administration conditions where the therapeutic monoclonal antibody specific for an tumor associated antigen is administered first, followed by the immune adjuvant, or conditions where the immune adjuvant is administered at the same time as the therapeutic monoclonal antibody specific for an tumor associated antigen. This also includes administration conditions where the immune adjuvant is a combination of compounds, and where a first drug may be administered, followed by the therapeutic monoclonal antibody specific for an tumor associated antigen, followed by a second drug; or where a first drug may be administered, followed by a second drug follow by the therapeutic monoclonal antibody specific for an tumor associated antigen; or where the therapeutic monoclonal antibody specific for an tumor associated antigen is administered first, followed by a first drug, followed by a second drug. Alternatively, all components of the treatment could be administered at the same time. Similar administration conditions could be used for other standard of care therapy including more than 2 drugs.

According to embodiments, the time sufficient for treatment of the patient with the immune adjuvant may be as defined above. In a particular embodiment, the time sufficient for treatment of the patient with the immune adjuvant may be about 3 weeks, or about 21 days.

According to embodiments, time between step b) and the final treatment may be from about 10 to about 14 weeks, or from about 10 to about 13 weeks, or about 10 to about 12 weeks, or about 10 to about 11 weeks, or about 11 to 14 weeks, or about 11 to 13 weeks, or about 11 to 12 weeks, or about 12 to 14 weeks, or about 12 to 13 weeks, or about 10 weeks, or about 11 weeks, or about 12 weeks, or about 13 weeks, or about 14 weeks, or about 2.5 month, about 3 months, about 3.5 months.

The inventors have unexpectedly discovered that monoclonal antibody specific for a tumor associated antigen in combination with an immune adjuvant can inhibit tumor growth. Without being bound by theory, the combination of monoclonal antibodies specific for a tumor associated antigen with the immune adjuvant in accordance with the invention appears to be protecting subjects against growth of tumors. The invention is unique and unexpected in that it provides for a synergistic effect between these two immune modulators to greatly enhance patient survival. This is in stark contrast to the use of chemotherapy alone followed by monoclonal antibodies specific for a tumor associated antigen alone after the initial chemotherapy treatment, which showed no improvements in clinical outcome in advanced ovarian cancer (Berek et al. J Clin Onc 27:418-425, 2009). This is also in contrast with the study of Braly et al. (J Immunother 2009; 32:54-65) which prescribed 8 cycles of chemotherapy including immunotherapy at cycles 1, 3, and 5; two additional rounds of chemotherapy and immunotherapy at 12 and 24 weeks past cycle 5, followed by follow-up additional immunotherapy (6 rounds) for up to two years—for a total of 11 doses of immunotherapy. The present invention includes a maximum of 6 cycles of immune adjuvant treatment (in this case, chemotherapy), combined with immunotherapy at cycles 1, 3 and 5, and a final round of immunotherapy alone at 12 past cycle 5, for a total of 4 rounds of immunotherapy, with no follow-up or maintenance therapy (See FIG. 1). Unexpectedly, the treatment dramatically improved clinical outcome in advanced ovarian cancer patients. In particular, a direct comparison may be made between the study of Braly et al., where the present invention display much improved progression-free survival.

A reduction in growth kinetics, or complete elimination of, a cancer tumor or a metastasized cell or tumor as used herein is defined to mean that which is as understood in the art. For example, a reduction in growth kinetics means a reduction in the exponential growth, specific growth rate, or doubling time of a primary solid tumor, metastasized cell, or metastasized tumor relative to the exponential growth, specific growth rate, or doubling time normally observed in vivo or in vitro for a given tumor type. Complete elimination of a tumor is the absence of tumor presence, either by symptoms, physical exam, or radiographic imaging, in the presence of the therapeutic monoclonal antibody specific for a tumor associated antigen in combination with at least one immunostimulatory compound, and at least one immune homeostatic checkpoint inhibitor, where a tumor was previously seen to be present by these detection methodologies.

According to an embodiment, antigen specific antibodies can be used to enhance T cell reactivity to self-antigens, especially in patients without mutations in human tumor associated antigens (TAA) that are identical with self. By binding self-antigens with low dose immunogenic antibodies, the pool of available tumor specific T cells is enhanced and checkpoint interference can lead to amplified immunity and enhanced clinical activity of the therapy.

The combined effect of the immune modulator results in the inhibition of tumor growth and/or the facilitation of tumor destruction, in whole or in part.

The term "therapeutic monoclonal antibody specific for a tumor associated antigen" as used in the invention is a monoclonal antibody that may be any suitable monoclonal antibody, such as for example an IgG, and/or an IgE (which comprises the human Fc epsilon (ε) constant region) and also comprises variable regions comprising at least one antigen binding region specific for a tumor-associated antigen (TAA) that is a cell surface antigen or a soluble cancer antigen located in the tumor microenvironment or otherwise in close proximity to the tumor being treated.

The terms "monoclonal antibody" or "monoclonal antibodies" as used herein refer to a preparation of antibodies of single molecular composition. A monoclonal antibody composition displays a single binding specificity and affinity for a particular epitope. The monoclonal antibodies of the present invention are preferably chimeric, humanized, or fully human in order to bind to human antibody receptors such as the human Fc epsilon receptors when the subject host is a human. Humanized and fully human antibodies are also useful in reducing immunogenicity toward the murine components of, for example, a chimeric antibody, when the host subject is human. Monoclonal antibodies may be prepared by standard techniques including, but not limited to, recombinantly and synthetically.

The term "chimeric monoclonal antibody" refers to antibodies displaying a single binding specificity, which have one or more regions derived from one antibody and one or more regions derived from another antibody. In one embodiment of the invention, the constant regions are derived from the human epsilon (ε) constant region (heavy chain) and human kappa or lambda (light chain) constant regions. The variable regions of a chimeric IgE monoclonal antibody of the invention are typically of non-human origin such as from rodents, for example, mouse (murine), rabbit, rat or hamster.

As used herein, "humanized" monoclonal antibodies comprise constant regions that are derived from human epsilon constant region (heavy chain) and human kappa or lambda (light chain) constant regions. The variable regions of the antibodies preferably comprise a framework of human origin and antigen binding regions (CDRs) of non-human origin.

Fully human or human-like antibodies may be produced through vaccination of genetically engineered animals such as mouse lines produced at Amgen) and Bristol-Myers Squibb which contain the human immunoglobulin genetic repertoire and produce fully human antibodies in response to vaccination. Further, the use of phage display libraries incorporating the coding regions of human variable regions which can be identified and selected in an antigen-screening assay to produce a human immunoglobulin variable region binding to a target antigen.

The term "antigen binding region" refers to that portion of an antibody as used in the invention which contains the amino acid residues that interact with an antigen and confer on the antibody its specificity and affinity for the antigen. The antibody region includes the "framework" amino acid residues necessary to maintain the proper confirmation of the antigen binding residues.

An "antigen" is a molecule or portion of a molecule capable of being bound by an antibody, which is additionally capable of inducing an animal to produce antibody capable of binding to an epitope of that antigen. An antigen can have one or more epitopes that are the same or different. In a preferred embodiment, the antibodies of the invention are specific for a single epitope. In one embodiment, the antigen is a capable of being bound by an antibody as used in the invention to form an immune complex that in combination with at least one immunostimulatory compound, and at least one immune homeostatic checkpoint inhibitor, is capable of inhibiting cancer tumor growth. In one embodiment, the antigen, on its own, may not be capable of stimulating an immune response for any number of reasons, for example, the antigen is a "self" antigen, not normally recognized by the immune system as requiring response or the immune system has otherwise become tolerant to the antigen and does not mount an immune response. In another embodiment, the antigen is MUC1.

The term "epitope" is meant to refer to that portion of an antigen capable of being recognized by and bound by an antibody at one or more of the antibody's binding regions. Epitopes generally comprise chemically active surface groupings of molecules such as amino acids or sugar side chains and have specific three-dimensional structure characteristics as well as specific charge characteristics. In one embodiment, an epitope of an antigen is a repetitive epitope. In one embodiment, an epitope of an antigen is a non-repetitive epitope.

Therefore, in embodiments, the therapeutic monoclonal antibody specific for a tumor associated antigen may be any suitable antibody. According to another embodiment, the therapeutic monoclonal antibody specific for a tumor associated antigen may be any suitable IgG and/or IgE antibody, or any other therapeutic isotypes. According to an embodiment, the tumor associated antigen may be CA125, folate binding protein (FBP), HER2/neu, MUC1 or PSA. According to another embodiment, the monoclonal antibody specific for a tumor associated antigen may be for example mAb-AR20.5, mAb-B43.13, mAb 3C6.hIgE, mAb-4H5.hIgE, mAb-AR47.47, as well as the mouse/human chimeric anti-PSA IgE containing the variable regions of AR47.47 described in Daniels-Wells et al. (BMC Cancer. 2013 Apr. 17; 13:195. doi: 10.1186/1471-2407-13-195). According to another embodiment, the therapeutic tumor associated antigen specific antibody may be a chimeric monoclonal antibody, a humanized monoclonal antibody or a fully human monoclonal antibody.

Methods for raising antibodies, such as murine antibodies to an antigen, and for determining if a selected antibody binds to a unique antigen epitope are well known in the art.

Screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. Many means are known in the art for detecting binding in an immunoassay and are within the scope of the present invention.

For preparation of monoclonal antibodies, any technique that provides for the production of antibody molecules by continuous cell lines in culture may be used (see, e.g., Antibodies—A Laboratory Manual, Harlow and Lane, eds., Cold Spring Harbor Laboratory Press: Cold Spring Harbor, N.Y., 1988). These include but are not limited to the hybridoma technique originally developed by Kohler and Milstein (1975, *Nature* 256:495-497), as well as the trioma technique, the human B-cell hybridoma technique (Kozbor et al., 1983, *Immunology Today*, 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, *Proc. Natl. Acad. Sci. U.S.A.*, 80:2026-2030) or by transforming human B cells with EBV virus in vitro (Cole et al., 1985, in Monoclonal Antibodies and Cancer Therapy, Alan R. Liss, pp. 77-96). In fact, according to the invention, techniques developed for the production of "chimeric antibodies" (Morrison et al., 1984, *J. Bacteriol.* 159: 870; Neuberger et al., 1984, *Nature* 312:604-608; Takeda et al., 1985, *Nature* 314: 452-454) by splicing the genes from a mouse antibody molecule specific for a polypeptide together with genes from a human antibody molecule of appropriate biological activity can be used; such antibodies are within the scope of this invention.

In one embodiment, therapeutic monoclonal antibodies specific for a tumor associated antigen in accordance with the present invention are expressed by a positive transfectoma which is identified by enzyme-linked immunosorbent assay (ELISA) and Western Blot. The positive transfectoma will be cloned by limited dilution for highest productivity and selected for antibody production. As used herein a "transfectoma" includes recombinant eukaryotic host cells expressing the antibody, such as Chinese hamster ovary (CHO) cells and NS/O myeloma cells. Such transfectoma methodology is well known in the art (Morrison, S. (1985) *Science*, 229:1202). Previously published methodology used to generate mouse/human chimeric or humanized antibodies has yielded the successful production of various human chimeric antibodies or antibody fusion proteins (Helguera G, Penichet ML., *Methods Mol. Med.* (2005) 109:347-74).

In general, chimeric mouse-human monoclonal antibodies (i.e., chimeric antibodies) can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted. (See Robinson et al., International Patent Publication PCT/US86/02269; Akira, et al., European Patent Application 184,187; Taniguchi, M., European Patent Application 171, 496; Morrison et al., European Patent Application 173,494; Neuberger et al.; Cabilly et al. U.S. Pat. No. 4,816,567; Cabilly et al., European Patent Application 125,023; Better et al. (1988 *Science*, 240:1041-1043); Liu et al. (1987) *PNAS*, 84:3439-3443; Liu et al., 1987, *J. Immunol.*, 139:3521-3526; Sun et al. (1987) *PNAS*, 84:214-218; Nishimura et al., 1987, *Canc. Res.*, 47:999-1005; Wood et al. (1985) *Nature*, 314:446-449; and Shaw et al., 1988, *J. Natl Cancer Inst.*, 80:1553-1559).

The chimeric antibody can be further humanized by replacing sequences of the Fv variable region which are not directly involved in antigen binding with equivalent sequences from human Fv variable regions. General reviews of humanized chimeric antibodies are provided by Morrison, S. L., 1985, *Science*, 229:1202-1207 and by Oi et al., 1986, *BioTechniques*, 4:214. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-GPII$_b$III$_a$ antibody producing hybridoma. The recombinant DNA encoding the chimeric antibody, or fragment thereof, can then be cloned into an appropriate expression vector. Suitable humanized antibodies can alternatively be produced by CDR substitution (U.S. Pat. No. 5,225,539; Jones et al. 1986 *Nature*, 321:552-525; Verhoeyan et al. 1988 *Science*, 239: 1534; and Beidler et al. 1988 *J. Immunol.*, 141:4053-4060).

In a preferred embodiment, the therapeutic monoclonal antibody specific for a tumor associated antigen is an antibody specific to CA125 (MUC16). The antibody specific to CA125 may be mAb-B43.13 (oregovomab).

As used herein, an "effective amount" of a therapeutic monoclonal antibody specific for a tumor associated antigen of the invention is that amount sufficient to recognize and bind the epitope of the TAA that is a cell surface antigen and induce, elicit, or enhance the referenced immune response in accordance with the invention.

In embodiments, the immune adjuvant may be a chemotherapeutic agent, an immunostimulatory compound, an immune homeostatic checkpoint inhibitor, or a combination thereof. According to an embodiment, the chemotherapeutic agent may be a platinum-based chemotherapy, such as for example cisplatin, carboplatin, oxaliplatin, nedaplatin, triplatin tetranitrate, phenanthriplatin, picoplatin, satraplatin, and combinations thereof. It may also be TAXOL® (paclitaxel), doxorubicin, topotecan, a poly(adenosine diphosphate-ribose) polymerase (PARP) inhibitor, or combinations of each of the above chemotherapeutic agents. Examples of PARP inhibitors include, but are not limited to olaparib (AZD-2281 or Lynparza™), niraparib (MK-4827), rucaparib (AG014699 or Rubraca™), talazoparib (BMN-673), veliparib (ABT-888), CEP 9722, E7016, and BGB-290. Also contemplated as chemotherapeutic agents are cytotoxic therapeutic agents which include, but are not limited to, angiogenesis inhibitors, antiproliferative agents, kinase inhibitors, receptor tyrosine kinase inhibitors, aurora kinase inhibitors, polo-like kinase inhibitors, bcr-abl kinase inhibitors, growth factor inhibitors, COX-2 inhibitors, non-steroidal anti-inflammatory drugs (NSAIDS), antimitotic agents, alkylating agents, antimetabolites, intercalating antibiotics, platinum containing agents, growth factor inhibitors, ionizing radiation, cell cycle inhibitors, enzymes, topoisomerase inhibitors, biologic response modifiers, immunologicals, antibodies, hormonal therapies, retinoids/deltoids plant alkaloids, proteasome inhibitors, HSP-90 inhibitors, histone deacetylase inhibitors (HDAC) inhibitors, purine analogs, pyrimidine analogs, MEK inhibitors, CDK inhibitors, ErbB2 receptor inhibitors, mTOR inhibitors and combinations thereof as well as other antitumor agents.

Angiogenesis inhibitors include, but are not limited to, EGFR inhibitors, PDGFR inhibitors, VEGFR inhibitors, TTE2 inhibitors, IGFIR inhibitors, matrix metalloproteinase 2 (MMP-2) inhibitors, matrix metalloproteinase 9 (MMP-9) inhibitors, thrombospondin analogs such as thrombospondin-1 and N—Ac-Sar-Gly-Val-D-allolle-Thr-Nva-He-Arg-Pro-NHCH2CH3 or a salt thereof and analogues of N—Ac-Sar-Gly-Val-D-allolle-Thr-Nva-Ile-Arg-PrO—NHCH2CH3 such as N—Ac-GlyVal-D-alle-Ser-Gln-Ile-Arg-ProNHCH2CH3 or a salt thereof.

Examples of EGFR inhibitors include, but are not limited to, Iressa (gefitinib), Tarceva (erlotinib or OSI-774), Icotinib, Erbitux (cetuximab), EMD-7200, ABX-EGF, HR3, IgA antibodies, TP-38 (IVAX), EGFR fusion protein, EGF-vaccine, anti-EGFr immunoliposomes and Tykerb (lapatinib).

Examples of PDGFR inhibitors include, but are not limited to, CP-673,451 and CP-868596.

Examples of VEGFR inhibitors include, but are not limited to, Avastin (bevacizumab), Sutent (sunitinib, SUI 1248), Nexavar (sorafenib, BAY43-9006), CP-547,632, axitinib (AG13736), Apatinib, cabozantinib, Zactima (vandetanib, ZD-6474), AEE788, AZD-2171, VEGF trap, Vatalanib (PTK-787, ZK-222584), Macugen, M862, Pazopanib (GW786034), ABT-869 and angiozyme.

Examples of thrombospondin analogs include, but are not limited to, TSP-I and ABT-510.

Examples of aurora kinase inhibitors include, but are not limited to, VX-680, AZD-1152 and MLN-8054. Example of polo-like kinase inhibitors include, but are not limited to, BI-2536.

Examples of bcr-abl kinase inhibitors include, but are not limited to, Gleevec (imatinib) and Dasatinib (BMS354825).

Examples of platinum containing agents includes, but are not limited to, cisplatin, Paraplatin (carboplatin), eptaplatin, lobaplatin, nedaplatin, Eloxatin (oxaliplatin) or satraplatin.

Examples of mTOR inhibitors includes, but are not limited to, CCI-779, rapamycin, temsirolimus, everolimus, RAD001, INK-128 and ridaforolimus.

Examples of HSP-90 inhibitors includes, but are not limited to, geldanamycin, radicicol, 17-AAG, KOS-953, 17-DMAG, CNF-101, CNF-1010, 17-AAG-nab, NCS-683664, Mycograb, CNF-2024, PU3, PU24FC1, VER49009, IPI-504, SNX-2112 and STA-9090.

Examples of histone deacetylase inhibitors (HDAC) includes, but are not limited to, Suberoylanilide hydroxamic acid (SAHA), MS-275, valproic acid, TSA, LAQ-824, Trapoxin, tubacin, tubastatin, ACY-1215 and Depsipeptide.

Examples of MEK inhibitors include, but are not limited to, PD325901, ARRY-142886, ARRY-438162 and PD98059.

Examples of CDK inhibitors include, but are not limited to, flavopyridol, MCS-5A, CVT-2584, seliciclib (CYC-202, R-roscovitine), ZK-304709, PHA-690509, BMI-1040, GPC-286199, BMS-387,032, PD0332991 and AZD-5438.

Examples of COX-2 inhibitors include, but are not limited to, CELEBREX™ (celecoxib), parecoxib, deracoxib, ABT-963, MK-663 (etoricoxib), COX-189 Lumiracoxib), BMS347070, RS 57067, NS-398, Bextra (valdecoxib), paracoxib, Vioxx (rofecoxib), SD-8381, 4-Methyl-2-(3,4-dimethylphenyl)-1-(4-sulfamoyl-phenyl-1H-pyrrole, T-614, JTE-522, S-2474, SVT-2016, CT-3, SC-58125 and Arcoxia (etoricoxib).

Examples of non-steroidal anti-inflammatory drugs (NSAIDs) include, but are not limited to, Salsalate (Amigesic), Diflunisal (Dolobid), Ibuprofen (Motrin), Ketoprofen (Orudis), Nabumetone (Relafen), Piroxicam (Feldene), Naproxen (Aleve, Naprosyn), Diclofenac (Voltaren), Indomethacin (Indocin), Sulindac (Clinoril), Tolmetin (Tolectin), Etodolac (Lodine), Ketorolac (Toradol) and Oxaprozin (Daypro).

Examples of ErbB2 receptor inhibitors include, but are not limited to, CP-724-714, CI-1033, (canertinib), Herceptin (trastuzumab), Om itarg (2C4, petuzumab), TAK-165, GW-572016 (lonafarnib), GW-282974, EKB-569, PI-166, dHER2 (HER2 Vaccine), APC8024 (HER2 Vaccine), anti-HER/2neu bispecific antibody, B7.her2IgG3, AS HER2 trifunctional bispecfic antibodies, mAB AR-209 and mAB 2B-1.

Examples of alkylating agents include, but are not limited to, nitrogen mustard N-oxide, cyclophosphamide, ifosfamide, trofosfamide, Chlorambucil, melphalan, busulfan, mitobronitol, carboquone, thiotepa, ranimustine, nimustine, temozolomide, AMD-473, altretamine, AP-5280, apaziquone, brostallicin, bendamustine, carmustine, estramustine, fotemustine, glufosfamide, KW-2170, mafosfamide, and mitolactol, carmustine (BCNU), lomustine (CCNU), Busulfan, Treosulfan, Decarbazine and Temozolomide.

Examples of antimetabolites include but are not limited to, methotrexate, 6-mercaptopurine riboside, mercaptopurine, uracil analogues such as 5-fluorouracil (5-FU) alone or in combination with leucovorin, tegafur, UFT, doxifluridine, carmofur, cytarabine, cytarabine ocfosfate, enocitabine, S-I, Alimta (premetrexed disodium, LY231514, MTA), Gemzar (gemcitabine), fludarabine, 5-azacitidine, capecitabine, cladribine, clofarabine, decitabine, eflornithine, ethnylcytidine, cytosine arabinoside, hydroxyurea, TS-I, melphalan, nelarabine, nolatrexed, ocfosate, disodium premetrexed, pentostatin, pelitrexol, raltitrexed, triapine, trimetrexate, vidarabine, vincristine, vinorelbine, mycophenolic acid, tiazofurin, Ribavirin, EICAR, hydroxyurea and deferoxamine.

Examples of antibiotics include intercalating antibiotics but are not limited to, aclarubicin, actinomycins such as actinomycin D, amrubicin, annamycin, adriamycin, bleomycin a, bleomycin b, daunorubicin, doxorubicin, elsamitrucin, epirbucin, glarbuicin, idarubicin, mitomycin C, nemorubicin, neocarzinostatin, peplomycin, pirarubicin, rebeccamycin, stimalamer, streptozocin, valrubicin, zinostatin and combinations thereof.

Examples of topoisomerase inhibiting agents include, but are not limited to, one or more agents selected from the group consisting of aclarubicin, amonafide, belotecan, camptothecin, 10-hydroxycamptothecin, 9-am inocamptothecin, diflomotecan, irinotecan HCL (Camptosar), edotecarin, epirubicin (Ellence), etoposide, exatecan, gimatecan, lurtotecan, orathecin (Supergen), BN-80915, mitoxantrone, pirarbucin, pixantrone, rubitecan, sobuzoxane, SN-38, tafluposide and topotecan.

Examples of antibodies include, but are not limited to, Rituximab, Cetuximab, Bevacizumab, Trastuzimab, specific CD40 antibodies and specific IGFIR antibodies, Examples of hormonal therapies include, but are not limited to, exemestane (Aromasin), leuprolide acetate, anastrozole (Arimidex), fosrelin (Zoladex), goserelin, doxercalciferol, fadrozole, formestane, tamoxifen citrate (tamoxifen), Casodex, Abarelix, Trelstar, finasteride, fulvestrant, toremifene, raloxifene, lasofoxifene, letrozole, flutamide, bicalutamide, megesterol, mifepristone, nilutamide, dexamethasone, predisone and other glucocorticoids.

Examples of retinoids/deltoids include, but are not limited to, seocalcitol (EB 1089, CB 1093), lexacalcitrol (KH 1060), fenretinide, Aliretinoin, Bexarotene and LGD-1550.

Examples of plant alkaloids include, but are not limited to, vincristine, vinblastine, vindesine and vinorelbine.

Examples of proteasome inhibitors include, but are not limited to, bortezomib (Velcade), MGI 32, NPI-0052 and PR-171.

Examples of immunologicals include, but are not limited to, interferons and numerous other immune enhancing agents. Interferons include interferon alpha, interferon alpha-2a, interferon, alpha-2b, interferon beta, interferon gamma-1a, interferon gamma-1 b (Actimmune), or interferon gamma-nl and combinations thereof. Other agents include filgrastim, lentinan, sizofilan, TheraCys, ubenimex, WF-10, aldesleukin, alemtuzumab, BAM-002, decarbazine, daclizumab, denileukin, gemtuzumab ozogamicin, ibritumomab, imiquimod, lenograstim, lentinan, melanoma vaccine (Corixa), molgramostim, OncoVAC-CL, sargaramostim, tasonermin, tecleukin, thymalasin, tositumomab, Virulizin, Z-100, epratuzumab, mitumomab, oregovomab, pemtumomab (Y-muHMFGI), Provenge (Dendreon), CTLA4 (cytotoxic lymphocyte antigen 4) antibodies and agents capable of blocking CTLA4 such as MDX-010.

Examples of biological response modifiers are agents that modify defense mechanisms of living organisms or biological responses, such as survival, growth, or differentiation of tissue cells to direct them to have anti-tumor activity. Such agents include krestin, lentinan, sizofrran, picibanil and ubenimex.

Examples of pyrimidine analogs include, but are not limited to, 5-Fluorouracil,

Floxuridine, Doxifluridine, Ratitrexed, cytarabine (ara C), Cytosine arabinoside, Fludarabine, and Gemcitabine.

Examples of purine analogs include but are not limited to, Mercaptopurine and thioguanine.

Examples of antimitotic agents include, but are not limited to, ABT-751, paclitaxel, docetaxel, epothilone D (KOS-862) and ZK-EPO.

In a preferred embodiment, the chemotherapeutic agent is a combination of carboplatin and TAXOL®. In another preferred embodiment, the therapeutic monoclonal antibody specific for a tumor associated antigen is mAb-B43.13 (oregovomab), and the chemotherapeutic agent is a combination of carboplatin and TAXOL®.

In embodiments, the immune adjuvant may also be an immunostimulatory compound. According to an embodiment, the present invention includes immunostimulatory compounds. Immunostimulatory compounds are compound having the capacity to stimulate or elicit an immune response. As used herein, the term relates to exemplary immunostimulatory compounds that include toll-like receptor (TLR) agonists (e.g., TLR3, TLR4, TLR7, TLR9), N-acetylmuramyl-L-alanine-D-isoglutamine (MDP), lipopolysaccharides (LPS), genetically modified and/or degraded LPS, alum, glucan, colony stimulating factors (e.g., EPO, GM-CSF, G-CSF, M-CSF, pegylated G-CSF, SCF, IL-3, IL6, PIXY 321), interferons (e.g., gamma-interferon, alpha-interferon), interleukins (e.g., IL-2, IL-7, IL-12, IL-15, IL-18), MHC Class II binding peptides, saponins (e.g., QS21), unmethylated CpG sequences, 1-methyl tryptophan, arginase inhibitors, cyclophosphamide, antibodies that block immunosuppressive functions (e.g., anti-CTLA4 antibodies, anti-TGF-beta, etc.), and mixtures of two or more thereof.

In one preferred embodiment the immunostimulatory compound is a TLR3 agonist. In preferred embodiments, the TLR3 agonist for use according to the invention is a double stranded nucleic acid selected from the group consisting of: polyinosinic acid and polycytidylic acid, polyadenylic acid and polyuridylic acid, polyinosinic acid analogue and polycytidylic acid, polyinosinic acid and polycytidylic acid analogue, polyinosinic acid analogue and polycytidylic acid analogue, polyadenylic acid analogue and polyuridylic acid, polyadenylic acid and polyuridylic acid analogue, and polyadenylic acid analogue and polyuridylic acid analogue. Specific examples of double-stranded RNA as TLR3 agonists further include Polyadenur (Ipsen) and Ampligen (Hemispherx). Polyadenur is a polyA/U RNA molecule, i.e., contains a polyA strand and a polyU strand. Ampligen is disclosed for instance in EP 281 380 or EP 113 162. In another preferred embodiment, the TLR3 agonist may be Poly (I:C)LC or polyIC (Hiltonol®), which is a synthetic complex of carboxymethylcellulose, polyinosinic-polycytidylic acid, and poly-L-lysine double-stranded RNA. Poly (I:C)LC may stimulate the release of cytotoxic cytokines and, by inducing interferon-gamma production, may increase the tumoricidal activities of various immunohematopoietic cells.

In one embodiment the immunostimulatory compound is a TLR4 agonist. Exemplary TLR4 agonists include taxanes such as paclitaxel and docetaxal, lipopolysaccharides (LPS); E. coli LPS; and P. gingivalis LPS.

As used herein, an "effective amount" of an immunostimulatory compound of the invention is that amount sufficient to induce, elicit, or enhance the referenced immune response in accordance with the invention.

According to another embodiment, the present invention includes immune homeostatic checkpoint inhibitors. Immune homeostatic checkpoint inhibitors are monoclonal antibodies (mAb) directed to immune checkpoint molecules, which are expressed on immune cells and mediate signals to attenuate excessive immune reactions. According to an embodiment, immune homeostasis checkpoint inhibition may be performed with inhibitory monoclonal antibodies directed at the inhibitory immune receptors CTLA-4, PD-1, and PDL-1. According to some embodiments, such inhibitors have emerged as successful treatment approaches for patients with advanced melanoma. According to an embodiment, the immune homeostatic checkpoint inhibitors may be one of an anti-CTLA-4, anti-PD-1, and/or anti-PDL-1 antibody. According to an embodiment, the anti-CTLA-4 antibody may be Ipilimumab or tremelimumab or combinations thereof. According to another embodiment, the anti-PDL-1 antibody may be B7-H1 antibody, BMS-936559 antibody, MPDL3280A (atezolizumab) antibody, MEDI-4736 antibody, MSB0010718C antibody or combinations thereof. According to another embodiment, the anti-PD-1 antibody may be Nivolumab antibody, pembrolizumab antibody, pidilizumab antibody or combinations thereof. In addition, PD-1 may also be targeted with AMP-224, which is a PD-L2-IgG recombinant fusion protein. Additional antagonists of inhibitory pathways in the immune response are being advanced through clinical development. IMP321 is a soluble LAG-3 Ig fusion protein and MHC class II agonist, which is used to increase an immune response to tumors. LAG3 is an immune checkpoint molecule. Lirilumab is an antagonist to the KIR receptor and BMS 986016 is an antagonist of LAG3. A third inhibitory checkpoint pathway is the TIM-3-Galectin-9 pathway that is also a promising target for checkpoint inhibition. RX518 targets and activates the glucocorticoid-induced tumor necrosis factor receptor (GITR), a member of the TNF receptor superfamily that is expressed on the surface of multiple types of immune cells, including regulatory T cells, effector T cells, B cells, natural killer (NK) cells, and activated dendritic cells.

As used herein, an "effective amount" of an immune homeostatic checkpoint inhibitor of the invention is that amount sufficient to induce, elicit, or enhance the referenced immune response in accordance with the invention.

According to an embodiment, the method of the present invention is for the treatment of any cancer, and preferably for the treatment of ovarian cancer.

According to yet another embodiment, the present invention also encompasses composition for use for inhibiting cancer tumor growth in a patient in need thereof, the composition comprising a therapeutic monoclonal antibody specific for a tumor associated antigen, at least one immune adjuvant.

Such compositions comprise a therapeutically effective amount of a therapeutic monoclonal antibody specific for a tumor associated antigen, and at least one immune adjuvant and may also include a pharmaceutically acceptable carrier. In one preferred embodiment, the pharmaceutical composition comprises a therapeutic monoclonal antibody that specifically binds to CA125.

In accordance with a method or use of the invention compositions comprising the therapeutic monoclonal antibody specific for a tumor associated antigen, the immune adjuvant of the invention may be administered to the patient by any immunologically suitable route. For example, they may be introduced into the patient by an intravenous, subcutaneous, intraperitoneal, intrathecal, intravesical, intradermal, intramuscular, or intralymphatic routes, alone or as combination. The composition may be in solution, tablet, aerosol, or multi-phase formulation forms. Liposomes, long-circulating liposomes, immunoliposomes, biodegradable microspheres, micelles, or the like may also be used as a carrier, vehicle, or delivery system. Furthermore, using ex vivo procedures well known in the art, blood or serum from the patient may be removed from the patient; optionally, it may be desirable to purify the antigen in the patient's blood; the blood or serum may then be mixed with a composition that includes a binding agent according to the invention; and the treated blood or serum is returned to the patient. The invention should not be limited to any particular method of introducing the binding agent into the patient.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the composition of the invention which will be effective in the treatment, inhibition and prevention of tumor growth associated with the antigen to which the antibody of the invention is specific can be determined by standard clinical techniques. The presence of the antibody in the extra vascular space, can be assayed by standard skin wheal and flair responses, in response to intradermal administration of purified antigen (e.g. CA125). In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For the antibodies used in the invention, the dosage administered to a patient is typically 0.001 µg/kg to 1 mg/kg of the patient's body weight. Preferably, the dosage administered to a patient is between 0.01 µg/kg and 0.1 mg/kg of the patient's body weight, more preferably 0.02 µg/kg to 20 µg/kg of the patient's body weight. Lower dosages of the antibodies of the invention and less frequent administration may also be possible.

For the chemotherapeutic agents used in the invention, the dosage administered to a patient may be according to the ranges or concentrations that have been optimized by their respective manufacturers.

For the immunostimulatory compound used in the invention, the dosage administered to a patient may be according to the ranges or concentrations that have been optimized by their respective manufacturers.

For the immune homeostatic checkpoint inhibitor used in the invention, the dosage administered to a patient may be according to the ranges or concentrations that have been optimized by their respective manufacturers.

In embodiments, each disease is treated according to standard of care treatment(s), where dosages of therapeutics administered to a patient may be according to the ranges or concentrations that have been optimized by their respective manufacturers.

The pharmaceutical compositions of the present invention have in vitro and in vivo diagnostic and therapeutic utilities. For example, these molecules can be administered to cells in culture, e.g., in vitro or ex vivo, or in a subject, e.g., in vivo, to treat cancer. As used herein, the term "subject" is intended to include human and non-human animals. A preferred subject is a human patient with cancer. As used herein the terms "treat" "treating" and "treatment" of cancer includes: preventing the appearance of tumor metastasis in a patient, inhibiting the onset of cancer in a patient; eliminating or reducing a preexisting tumor burden in a patient either with metastatic cancer or cancer localized to the organ of origin; prolonging survival in a cancer patient; prolonging the remission period in a cancer patient following initial treatment with chemotherapy and/or surgery; and/or prolonging any period between cancer remission and cancer relapse in a patient.

When used for therapy for the treatment of cancer, the antibodies used in the invention are administered to the patient in therapeutically effective amounts (i.e. amounts needed to treat clinically apparent tumors, or prevent the appearance of clinically apparent tumor, either at the original site or a distant site, at some time point in the future). The antibodies used in the invention and the pharmaceutical compositions containing them will normally be administered parenterally, when possible, or at the target cell site, or intravenously.

According to yet another embodiment, the present invention also encompasses kits for use for inhibiting cancer tumor growth in a patient in need thereof. The kits may comprise a therapeutic monoclonal antibody specific for a tumor associated antigen, at least one immunostimulatory compound, at least one immune homeostatic checkpoint inhibitor, and instructions on how to use the kit.

The present invention will be more readily understood by referring to the following examples which are given to illustrate the invention rather than to limit its scope.

Example 1

Combining Front Line Chemotherapy and Immunotherapy

Now referring to FIG. 1, which is a schematic of the Frontline Chemoimmunotherapy Randomized Phase II trial according to an embodiment of the present invention.
Design:
Phase II Randomized trial (centers in US and Italy).
Patients:
Initial treatment of newly diagnosed optimally debulked stage III/IV Ovarian cancer expressing CA125 (MUC16) at least 2× normal at baseline.
Treatment:
Standard of care (SOC) chemotherapy (6 cycles IV carboplatin-paclitaxel) (Control) vs SOC chemotherapy plus oregovomab immunotherapy (IT) (CIT)
Schedule:
In CIT group oregovomab is administered at cycles 1, 3, 5 in combination with the SOC chemotherapy, as well as at cycle 5 plus 12 weeks as a single oregovomab immunotherapy immunization (without SOC chemotherapy). Initial Analysis post completion of treatment phase. Final Analysis post 3 year follow up.
Endpoints:
Safety, Immune Response and Clinical Outcomes (TTCR, PFS and OS).
A total of 97 patients were enrolled in the intent to treat (ITT) population.
Oreqovomab MAb-B43.13
All patients in the CIT group enrolled in this study were to receive single IV doses of MAb-B43.13 containing 2 mg of the monoclonal antibody concurrent with conventional chemotherapy Cycles 1, 3 and 5. Subsequently all patients in the CIT group were to receive single IV doses of MAb-B43.13 at Cycle 5+12 weeks in the post-chemotherapy phase (without concurrent chemotherapy).

The lyophilized contents of a vial of MAb-B43.13 were to be dissolved in 2 mL of 0.9% Sodium Chloride Injection USP (or equivalent). The vial contents were to be mixed by gentle swirling to avoid the formation of foam and then examined to ensure that the solution was free of foreign or particulate matter. The resulting solution was to be withdrawn from the vial with a suitable needle and syringe and added to 50 mL of 0.9% Sodium Chloride Injection USP (or equivalent) in a small (50 mL) infusion bag.

Each dose of MAb-B43.13 (containing 2 mg of MAb-B43.13 in 50 mL of Sodium Chloride Injection USP) was to be administered to the patient by slow (20 minutes) IV infusion in an appropriate treatment area. The dose of MAb-B43.13 was to be administered after paclitaxel but prior to carboplatin.

Chemotherapy

Maximum body surface area (BSA) used for chemotherapy dose calculations was to be determined per acceptable standard (e.g., Gynecologic Oncology Group Chemotherapy Procedures Manual). Maximum creatinine clearance was to be 120 mL/min for the purpose of this study.
Paclitaxel Paclitaxel is supplied as a sterile solution concentrate, 6 mg/mL, in 5 mL vials (30 mg/vial) or 17 mL vials (100 mg/vial) in polyoxyethylated castor oil (Cremophor EL) 50% and dehydrated alcohol, USP, 50%, was to be used for this trial. The appropriate dose of paclitaxel was to be diluted in 500-1000 mL of 9% Sodium Chloride injection, USP or 5% Dextrose injection, USP (D5W). Paclitaxel was to be prepared in glass or polyolefin containers due to leaching of diethylhexylphthalate plasticizer from polyvinyl chloride (PVC) bags and intravenous tubing by the Cremophor vehicle in which paclitaxel is solubilized.

Paclitaxel, at a dose of 175 mg/m$^2$, was to be administered via an infusion control device (pump) using non-PVC tubing and connectors, as a 3-hour continuous IV infusion. In-line filtration was necessary for administration of paclitaxel solutions. Due to the risk of immediate hypersensitivity reaction, paclitaxel should always be the first drug to be infused during any combination.
Carboplatin Carboplatin is supplied as a sterile lyophilized powder available in single-dose vials containing 50 mg, 150 mg and 450 mg of carboplatin for administration by IV infusion. Each vial contains equal parts by weight of carboplatin and mannitol.

Immediately prior to use, the contents of each vial was to be reconstituted with either sterile water for injection, USP, 5% dextrose in water, or 9% sodium chloride injection, USP, according to the following schedule: 50 mg vial with 5 mL, 150 mg vial with 15 mL and 450 mg vial with 45 mL, all producing a concentration of 10 mg/m L.

The dose of carboplatin was to be calculated to reach a target area under the curve (AUC) of concentration×time of 6 according to the Calvert formula using an estimated glomerular filtration rate (GFR) from the Jelliffe formula for creatinine clearance (CrCl).

Calvert Formula: Carboplatin dose (mg)=target AUC×(GFR+25)

For the purposes of this protocol, the GFR was considered to be equivalent to the CrCl. The creatinine clearance was to be estimated by the method of Jelliffe using the following formula:

$$CrCl = 0.9 \times \frac{[98 - (0.8(Age - 20))]}{\text{Serum Creatinine}}$$

Where: CrCl=estimated creatinine clearance in mL/min; Age=patient's age in years; serum creatinine in mg/dL.

The initial dose of carboplatin was to be calculated using GFR. In the absence of new renal obstruction or other renal toxicity (i.e., serum creatinine>1.5×ULN), the dose of carboplatin was not to be recalculated for subsequent cycles, but was to be subject to dose modification for hematologic criteria and other events.

In patients with an abnormally low serum creatinine, due to reduced protein intake and/or low muscle mass, the creatinine clearance (CrCl) was to be determined from a 24 hour urine collection, rather than a Jelliffe formula.

Carboplatin was to be administered as a 30 minute IV infusion. When administered in conjunction with other medications, carboplatin was to be infused after the other agents.

TABLE 1

Demographics analysis of the ITT population

| | | ITT Population | | |
|---|---|---|---|---|
| | | Treatment Arm 1 CIT (N = 47) | Treatment Arm 2 SOC (N = 50) | All (N = 97) |
| Age (years) | n | 47 | 50 | 97 |
| | Mean (SD) | 57.9 (11.4) | 58.1 (10.4) | 58.0 (10.8) |
| | Median | 58.3 | 57.6 | 57.8 |
| | Mann-Whitney-Wilcoxon p-value | 0.9971 | | |
| Race | African | 0 | 1 (2.0%) | 1 (1.0%) |
| | White | 47 (100%) | 49 (98.0%) | 96 (99.0%) |
| | Other | 0 | 0 | 0 |
| | Fisher p-value | 1.0000 | | |
| ECOG performance status | 0 | 39 (83.0) | 46 (92.0%) | 85 (87.6%) |
| ECOG performance status | 1 | 8 (17.0%) | 4 (8.0%) | 12 (12.4%) |
| | Chi-square p-value | 0.1775 | | |

TABLE 2

Ovarian Cancer Characteristics in the ITT

| | | ITT Population | | |
|---|---|---|---|---|
| | | Treatment Arm 1 (N = 47) | Treatment Arm 2 (N = 50) | All (N = 97) |
| Time from diagnosis to randomization (years) | n | 47 | 49 | 96 |
| | n. missing | 0 | 1 | 1 |
| | Median (Min, Max) | 0.10 (0.01, 0.16) | 0.11 (0.04, 0.36) | 0.10 (0.01, 0.36) |
| | Mann-Whitney-Wilcoxon p-value | 0.4813 | | |
| Tumor grade | 0 | 0 (0.0%) | 0 (0.0%) | 0 (0.0%) |
| | 1 | 0 (0.0%) | 0 (0.0%) | 0 (0.0%) |
| | 2 | 6 (12.8%) | 4 (8.0%) | 10 (10.3%) |
| | 3 | 40 (85.1%) | 44 (88.0%) | 84 (86.6%) |
| | 4 | 1 (2.1%) | 0 (0.0%) | 1 (1.0%) |
| | Unknown | 0 (0.0%) | 2 (4.0%) | 2 (2.1%) |
| | Fisher p-value | 0.3234 | | |
| Histology | Mucinous | 1 (2.13%) | 1 (2.0%) | 2 (2.1%) |
| | Serous | 42 (89.4%) | 44 (88.0%) | 86 (88.7%) |
| | Undifferentiated | 0 (0.0%) | 0 (0.0%) | 0 (0.0%) |
| | Endometroid | 4 (8.5%) | 2 (4.0%) | 6 (6.2%) |
| | Clear Cell | 0 (0.0%) | 2 (4.0%) | 2 (2.1%) |
| | Other | 0 (0.0%) | 1 (2.%) | 1 (1.0%) |
| | Fisher p-value | 0.6041 | | |
| Organ of origin | Ovary | 42 (89.4%) | 43 (86.0%) | 85 (87.6%) |
| | Fallopian Tube | 3 (6.4%) | 2 (4.0%) | 5 (5.2%) |
| | Peritoneum | 0 (0.0%) | 4 (8.0%) | 4 (4.1%) |
| | Ovary + Fallopian Tube | 1 (2.1%) | 1 (2.0%) | 2 (2.1%) |
| | Missing | 1 (2.1%) | 0 (0.0%) | 1 (1.0%) |
| | Fisher p-value | 0.2488 | | |
| FIGO stage | III | 1 (2.1%) | 2 (4.0%) | 3 (3.1%) |
| | IIIA | 5 (10.6%) | 3 (6.0%) | 8 (8.3%) |
| | IV | 5 (10.6%) | 3 (6.0%) | 8 (8.3%) |

TABLE 2-continued

Ovarian Cancer Characteristics in the ITT

| | | ITT Population | | |
|---|---|---|---|---|
| | | Treatment Arm 1 (N = 47) | Treatment Arm 2 (N = 50) | All (N = 97) |
| IIIB | | 9 (19.2%) | 3 (6.0%) | 12 (12.4%) |
| IIIC | | 27 (57.5%) | 39 (78.0%) | 66 (68.0%) |
| Missing | | 0 (0.0%) | 0 (0.0%) | 0 (0.00%) |
| Fisher p-value | | 0.1508 | | |

TABLE 3

Summary of adverse events

| | Safety Population | | |
|---|---|---|---|
| | Treatment Arm 1 CIT (N = 46) | Treatment Arm 2 SOC (N = 49) | All (N = 95) |
| Patients with any adverse event | 38 (82.6%) | 40 (81.6%) | 78 (82.1%) |
| Patients with any related adverse event | 8 (17.4%) | 9 (18.4%) | 17 (17.9%) |
| Patients with any serious adverse event | 10 (21.7%) | 8 (16.3%) | 18 (19.0%) |
| Patients with any serious related adverse event | 0 (0.0%) | 0 (0.0%) | 0 (0.0%) |
| Patients with any grade 3-4 adverse event | 24 (52.2%) | 28 (57.1%) | 52 (54.7%) |
| Patients with any grade 3-4 related adverse event | 2 (4.4%) | 4 (8.2%) | 6 (6.3%) |
| Patients with any adverse event leading to study drug discontinuation (*) | 3 (6.5%) | 1 (2.0%) | 4 (4.2%) |
| Patients with any adverse event leading death | 1 (2.2%) | 1 (2.0%) | 2 (2.1%) |

(*) Patients with permanent discontinuation

Oregovomab plus chemotherapy has similar adverse events profile to chemotherapy alone.

TABLE 4

Preliminary Clinical Data

| | | All patients | | |
|---|---|---|---|---|
| | | Treatment Arm 1 CIT (N = 47) | Treatment Arm 2 SOC (N = 50) | All (N = 97) |
| Relapse Data | | | | |
| Patients with clinical relapse | Yes | 14 (29.8%) | 29 (58.0%) | 43 (44.3%) |
| | No | 33 (70.2%) | 21 (42.0%) | 54 (55.7%) |
| | Chi-square p-value | 0.0052 | | |

TABLE 5

Progression free survival (PFS) data maturation

| | | All patients | |
|---|---|---|---|
| | | Treatment Arm 1 CIT (N = 47) | Treatment Arm 2 SOC (N = 50) |
| Censor summary | Total: | 47 | 49 |
| | Censors: | 30 (63.8%) | 17 (34.7%) |
| | Events: | 17 (36.2%) | 32 (65.3%) |
| Quartiles estimation | 75th percentile | [—] | 33.95 [18.74-] |
| | 50th percentile | [21.30-] | 15.39 [10.93-19.33] |
| | 25th percentile | 19.18 [9.98-28.59] | 9.35 [7.12-11.11] |
| Time to event estimation Survival time | Mean (SD) | 24.76 (1.38) | 18.67 (1.73) |
| | 0 month | 100.00 [100.00-100.00] | 100.00 [100.00-100.00] |
| | 6 months | 97.78 [85.25-99.68] | 91.66 [79.28-96.79] |
| | 12 months | 84.13 [69.57-92.10] | 57.55 [42.25-70.17] |
| | 18 months | 75.04 [59.47-85.33] | 42.53 [28.30-56.04] |

TABLE 5-continued

Progression free survival (PFS) data maturation

| | | All patients | |
|---|---|---|---|
| | | Treatment Arm 1 CIT (N = 47) | Treatment Arm 2 SOC (N = 50) |
| | 24 months | 65.30 [49.09-77.47] | 33.25 [20.17-46.90] |
| | 30 months | 61.46 [44.43-74.67] | 33.25 [20.17-46.90] |
| | 36 months | 56.34 [37.89-71.23] | 16.63 [1.80-44.87] |
| | 42 months | 56.34 [37.89-71.23] | [—] |
| | 48 months | [—] | [—] |
| Log-rank test | Pr > Chi-Square | 0.0009 | |

TABLE 6

Early Survival Data

| | | All patients | |
|---|---|---|---|
| Overall Survival ITT | | Treatment Arm 1 CIT (N = 47) | Treatment Arm 2 SOC (N = 50) |
| Censor summary | Total: | 46(*) | 49 |
| | Censors: | 42 (91.3%) | 33 (67.3%) |
| | Events: | 4 (8.7%) | 16 (32.7%) |
| Quartiles | 75th percentile | [—] | [38.34-] |
| estimation | 50th percentile | [—] | 38.34 [26.45-] |
| | 25th percentile | [30.91-] | 21.18 [11.33-38.34] |
| Time to event | Mean (SD) | 29.32 (1.04) | 29.89 (1.88) |
| estimation | 0 month | 100.00 [100.00-100.00] | 100.00 [100.00-100.00] |
| Survival time | 6 months | 97.73 [84.94-99.68] | 95.87 [84.49-98.95] |
| | 12 months | 93.07 [80.04-97.71] | 87.30 [73.88-94.09] |
| | 18 months | 93.07 [80.04-97.71] | 78.39 [63.51-87.76] |
| | 24 months | 93.07 [80.04-97.71] | 73.37 [57.73-83.98] |
| | 30 months | 93.07 [80.04-97.71] | 66.67 [49.62-79.09] |
| | 36 months | 87.60 [67.52-95.63] | 57.14 [33.49-75.11] |
| | 42 months | 87.60 [67.52-95.63] | 42.86 [15.14-68.37] |
| | 48 months | 87.60 [67.52-95.63] | [—] |
| Log-rank test | Pr > Chi-Square | 0.0025 | |

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A method for improving likelihood of survival in a stage III-IV ovarian cancer patient, the method comprising:
   (a) administering to a stage III-IV ovarian cancer patient 6 cycles of chemotherapy, wherein in each cycle the patient is administered a platinum-based chemotherapy and a taxane on the same day;
   (b) administering to the patient monoclonal antibody mAb-B43.13 concurrently during cycles 1, 3, and 5 of the 6 cycles of chemotherapy; and
   (c) administering to the patient in a final dose of monoclonal antibody mAb-B43.13 without concurrent chemotherapy about 10 to about 14 weeks after cycle 5 of the 6 cycles of chemotherapy,
   thereby increasing the patient's likelihood of survival in comparison with a control patient who has been diagnosed with stage III-IV ovarian cancer and has received treatment consisting of 6 cycles of chemotherapy consisting of said platinum-based chemotherapy and said taxane administration,
   wherein the method comprises no other treatment step in which mAb-B43.13, said platinum-based chemotherapy, or said taxane is administered to the patient, and wherein in step (b) said taxane, said platinum-based chemotherapy, and mAb-B43.13 are administered in this order on the same day.

2. The method of claim 1, wherein time interval between every two consecutive cycles of the 6 cycles of chemotherapy is 1 week, 2 weeks, or 1 month.

3. The method of claim 1, wherein time interval between every two consecutive cycles of the 6 cycles of chemotherapy is 3 weeks.

4. The method of claim 1, wherein step (c) is performed about 12 weeks after cycle 5 of the 6 cycles of chemotherapy.

5. The method of claim 1, wherein each of said mAb-B43.13, platinum-based chemotherapy, and taxane is intravenously administered.

6. The method of claim 1, wherein 2 mg of mAb-B43.13 is administered in a volume of 50 ml by a 20-minute infusion.

7. The method of claim 1, wherein said platinum-based chemotherapy comprises cisplatin, carboplatin, oxaliplatin, nedaplatin, triplatin tetranitrate, phenanthriplatin, picoplatin, satraplatin, or combinations thereof.

8. The method of claim 7, wherein said platinum-based chemotherapy is carboplatin.

9. The method of claim 1, wherein said taxane is paclitaxel, docetaxel, or a combination thereof.

10. The method of claim 9, wherein said taxane is paclitaxel.

11. The method of claim 1, wherein step (c) comprises no follow-up therapy.

* * * * *